US011078277B2

(12) United States Patent
Levade et al.

(10) Patent No.: US 11,078,277 B2
(45) Date of Patent: Aug. 3, 2021

(54) METHODS AND PHARMACEUTICAL COMPOSITIONS FOR ENHANCING CD8+ T CELL-DEPENDENT IMMUNE RESPONSES IN SUBJECTS SUFFERING FROM CANCER

(71) Applicants: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

(72) Inventors: Thierry Levade, Toulouse (FR); Bruno Segui, Toulouse (FR); Florie Bertrand, Toulouse (FR); Julia Rochotte, Toulouse (FR); Anne Montfort, Toulouse (FR); Nathalie Andrieu-Abadie, Toulouse (FR); Celine Colacios Viatge, Toulouse (FR); Nicolas Meyer, Toulouse (FR)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 214 days.

(21) Appl. No.: 16/074,555

(22) PCT Filed: Feb. 1, 2017

(86) PCT No.: PCT/EP2017/052172
§ 371 (c)(1),
(2) Date: Aug. 1, 2018

(87) PCT Pub. No.: WO2017/134116
PCT Pub. Date: Aug. 10, 2017

(65) Prior Publication Data
US 2019/0031756 A1 Jan. 31, 2019

(30) Foreign Application Priority Data

Feb. 2, 2016 (EP) .................................... 16305107
Sep. 12, 2016 (EP) .................................... 16306143

(51) Int. Cl.
| | |
|---|---|
| A61K 48/00 | (2006.01) |
| A61P 35/00 | (2006.01) |
| C12N 15/86 | (2006.01) |
| C07K 16/28 | (2006.01) |
| A61K 38/46 | (2006.01) |
| A61K 31/713 | (2006.01) |
| A61K 39/00 | (2006.01) |
| A61K 9/127 | (2006.01) |
| C12N 9/16 | (2006.01) |
| G01N 33/569 | (2006.01) |

(52) U.S. Cl.
CPC .......... *C07K 16/2815* (2013.01); *A61K 9/127* (2013.01); *A61K 31/713* (2013.01); *A61K 38/465* (2013.01); *A61K 39/001111* (2018.08); *A61P 35/00* (2018.01); *C07K 16/2818* (2013.01); *C12N 9/16* (2013.01); *C12Y 301/04012* (2013.01); *G01N 33/56972* (2013.01); *A61K 2039/505* (2013.01); *G01N 2333/70517* (2013.01)

(58) Field of Classification Search
CPC ........ C12N 15/86; C12N 15/10; A61K 48/00; A61P 35/00
See application file for complete search history.

(56) References Cited

U.S. PATENT DOCUMENTS

2012/0252883 A1* 10/2012 Kolesnick .............. A61K 45/06
514/44 R

FOREIGN PATENT DOCUMENTS

DE 199 38 671 A1 2/2001

OTHER PUBLICATIONS

Kim et al. 2014; Combining targeted therapy and immune checkpoint inhibitors in the treatment of metastatic melanoma. Cancer Biol. Med. 11:237-246.*
Oskoulan et al. 2010; Cancer treatment strategies targeting sphingolipid metabolism. Adv Exp Med. Biol 688: 185-205.*
Twyman-Saint Victor et al. published Mar. 9, 2015; Radiation and dual checkpoint blockade activate non-redundant immune mechanisms in cancer. Nature. 520: 373-377 plus Online Content comprising methods and Extended Data pp. 1-13.*
Goncalves et al. 2017; Gene therapy: advances, challenges and perspectives. Einstein 14(3): 369-375.*
Goswami et al. 2019; Gene therapy leaves a vicious cycle. Frontiers in Oncology. 9; Article 297, pp. 1-25.*
Rochotte et al: "Role of neutral sphingomyelinase 2 and the sphingomyelin/ceramide pathway in B16 melanoma growth", Sphingolipid Club, Scientific Board.

(Continued)

*Primary Examiner* — Karen Cochrane Carlson
(74) *Attorney, Agent, or Firm* — W&C IP

(57) ABSTRACT

The present invention relates to methods and pharmaceutical compositions for enhancing CD8+ T cell-dependent immune responses in subjects suffering from cancer. In particular, the present invention relates to a method of enhancing the CD8+ T cell-dependent immune response in a subject suffering from cancer comprising administering to the subject a therapeutically effective amount of an agent capable of increasing intra-tumoral ceramide content.

Figure 1:
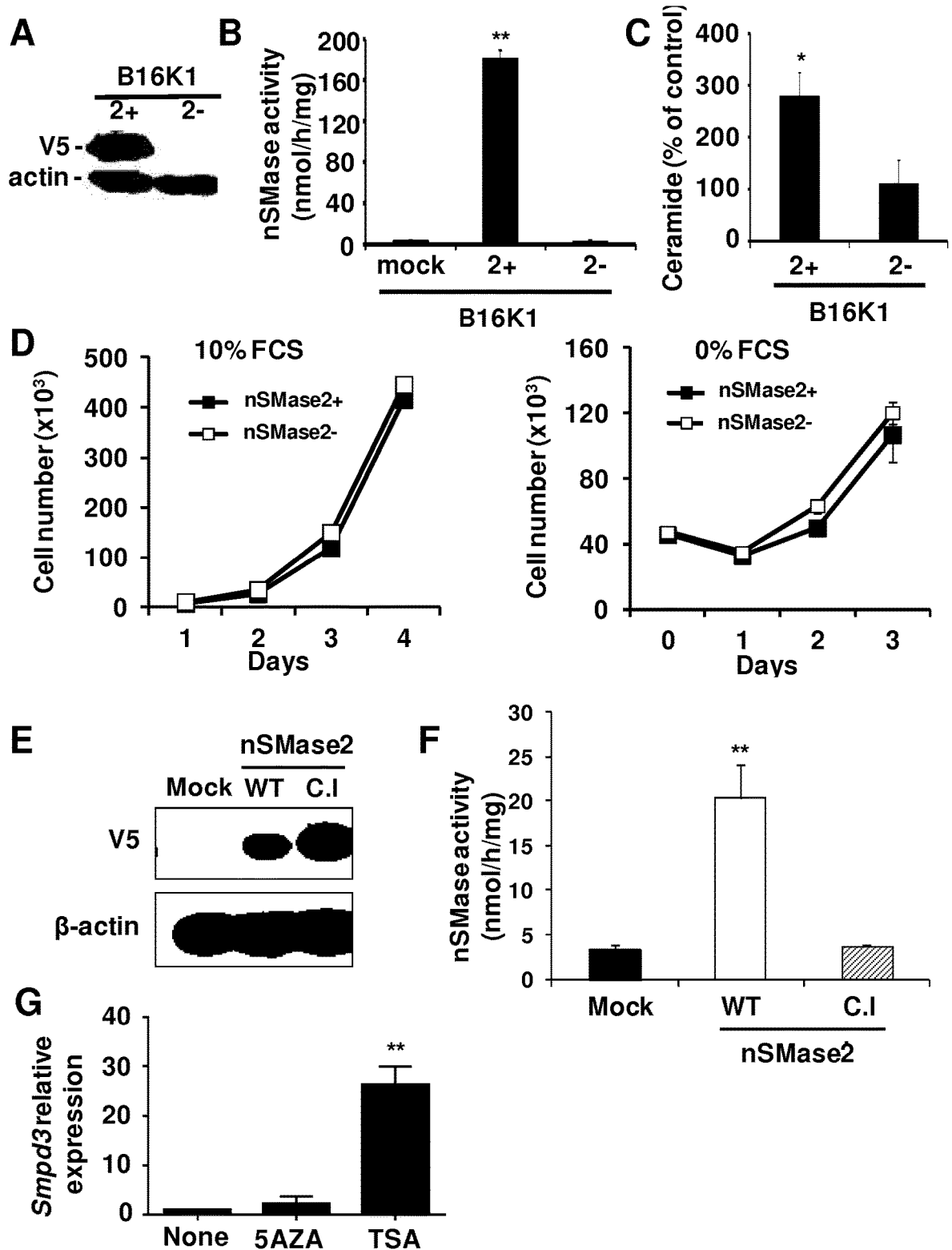

8 Claims, 10 Drawing Sheets
Specification includes a Sequence Listing.

(56) References Cited

OTHER PUBLICATIONS

Bonggoo Park et al: "Neutral sphingomyelinase 2 modulates cytotoxic effects of protopanaxadiol on different human cancer cells", BMC Complementary and Alternative Medicine, Biomed Central Ltd., London, GB, vol. 13, No. 1, p. 194, Jul. 27, 2013.

N. Kosaka et al: "Secretory Mechanisms and Intercellular Transfer of MicroRNAs in Living Cells", Journal of Biological Chemistry, vol. 285, No. 23, pp. 17442-17452, Jun. 4, 2010.

Abo Bakr Abdel Shakor et al: "Curcumin induces apoptosis of multidrug-resistant human leukemia HL60 cells by complex pathways leading to ceramide accumulation", Biochimica and Biophysica Acta. Molecular and Cell Biology of Lipids, vol. 1841, No. 12, pp. 1672-1682, Dec. 1, 2014.

A A Shamseddine et al: "P53-dependent upregulation of neutral sphingomyelinaase-2: role in doxorubicin-induced growth arrest", Cell Death and Disease, vol. 6, No. 10, p. e1947, Oct. 29, 2015.

Qin Jungdong et al: "The hyaluronic acid inhibitor 4-methylumbelliferone is an NSMase2 activator-role of Ceramide in MU antitumor activity", Biochimica and Biophysica Acta. Molecular and Cell Biology of Lipids, vol. 1861, No. 2, pp. 78-90, Nov. 5, 2015.

\* cited by examiner

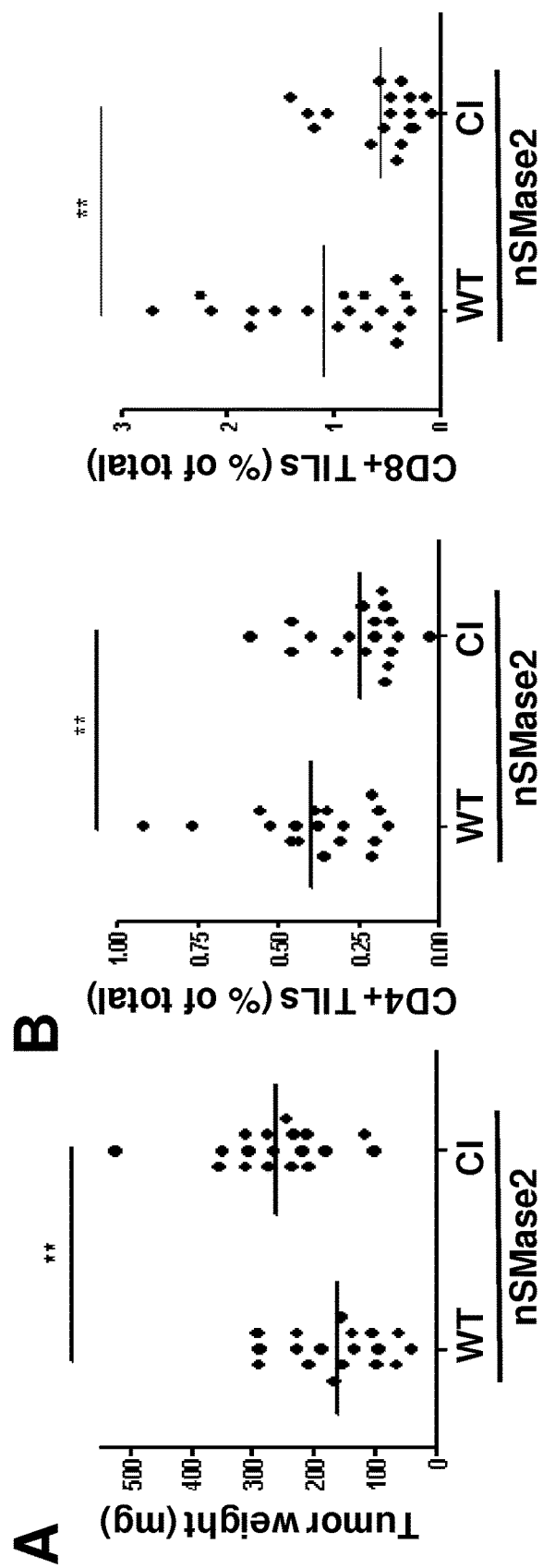
Figure 3 A and B

C
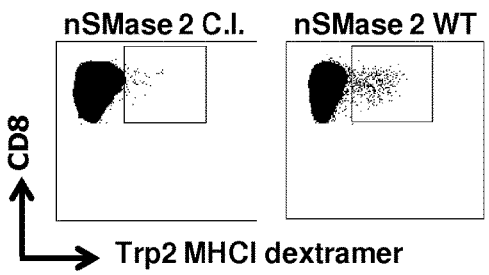
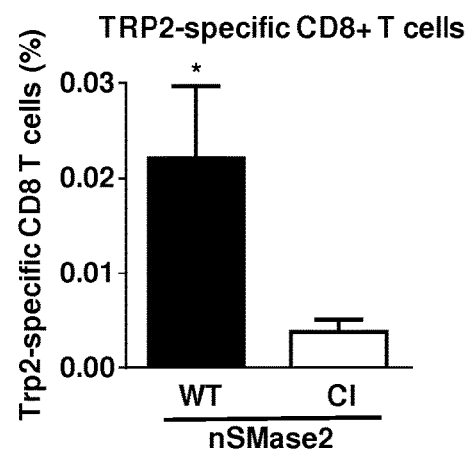
D
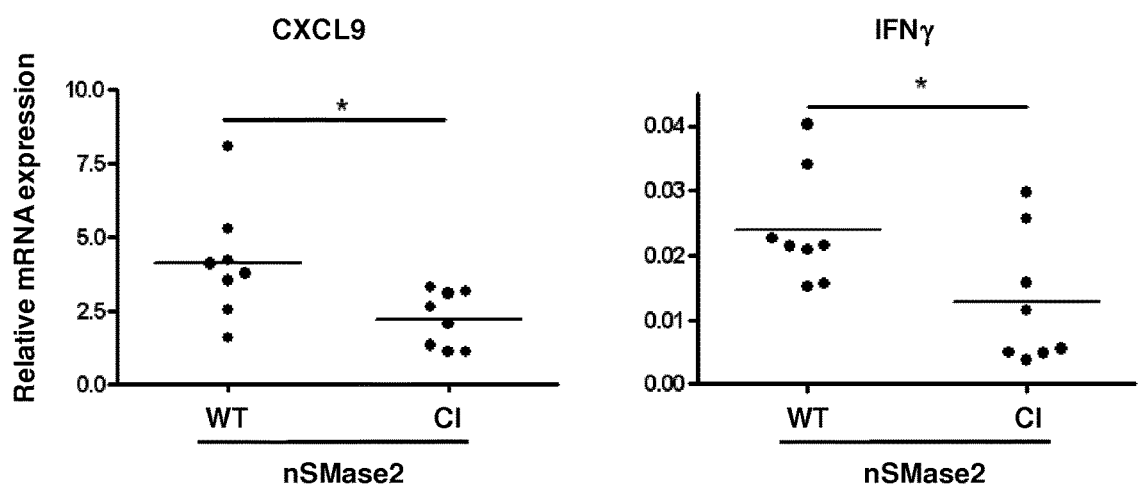
Figure 3 C and D
A
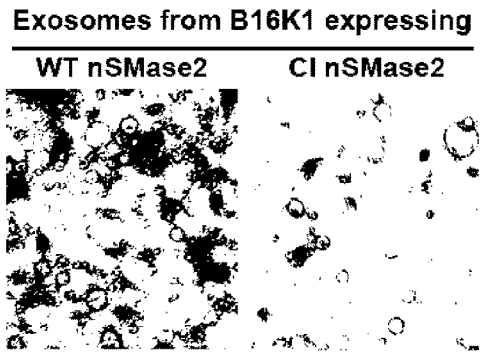
B
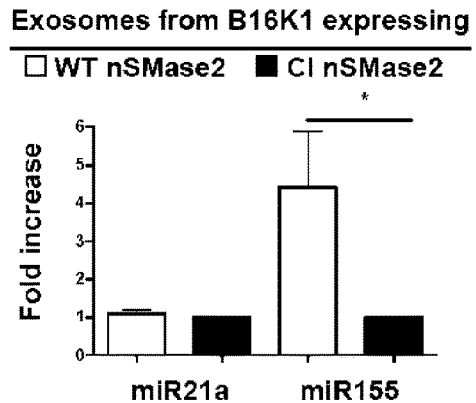
Figure 4 A and B

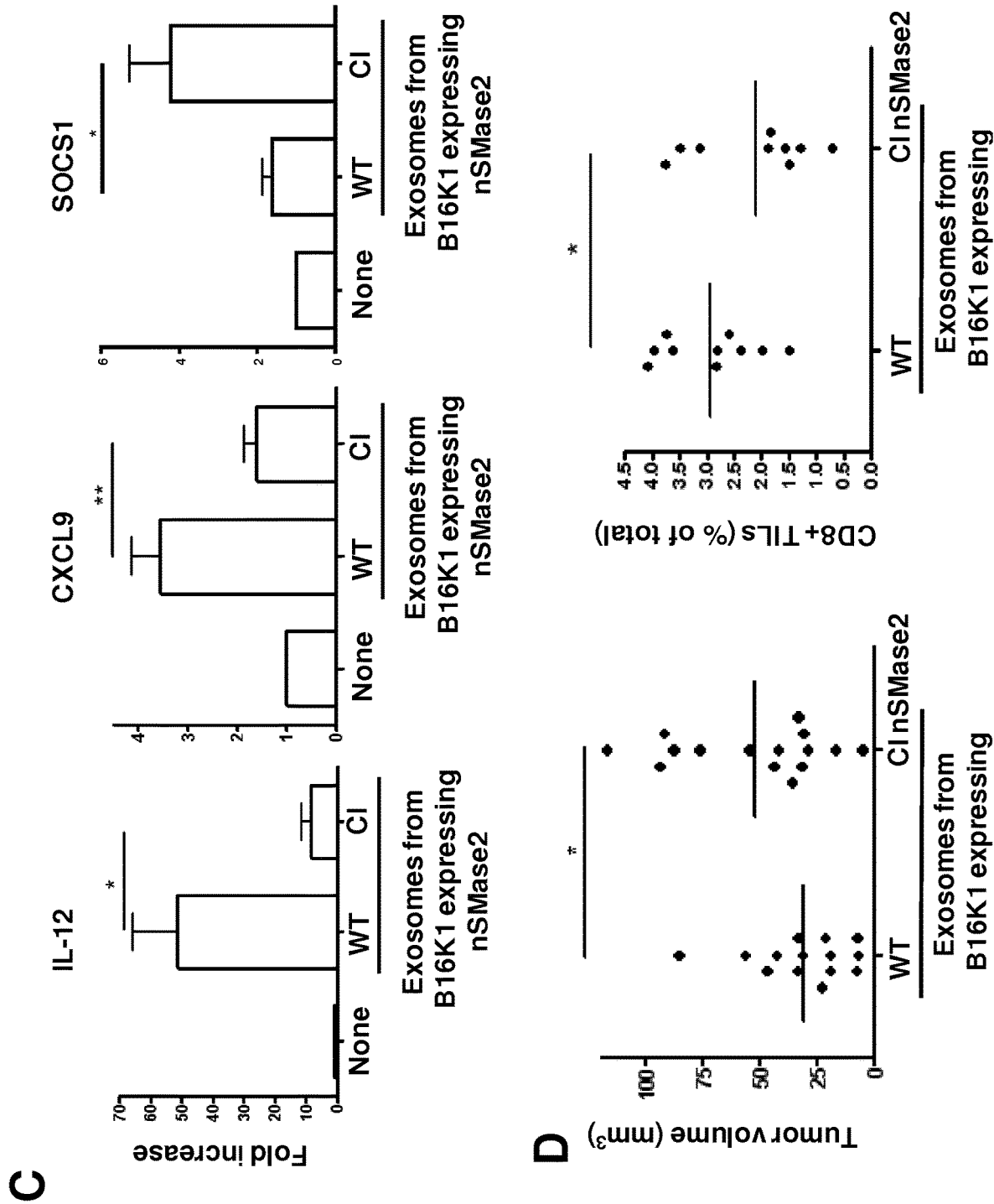
Figure 4 C and D

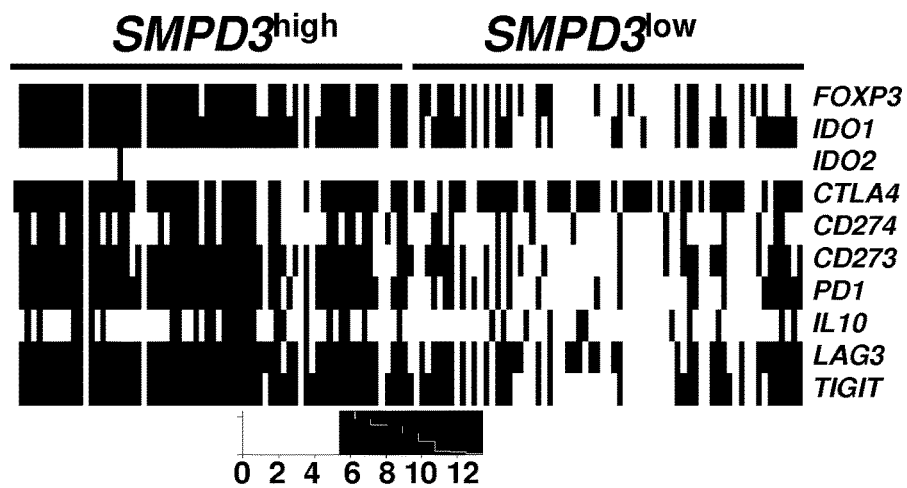
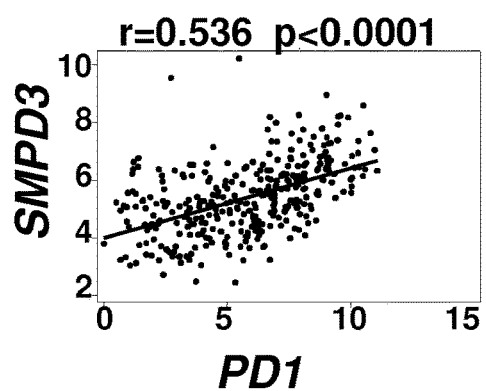
Figure 7A
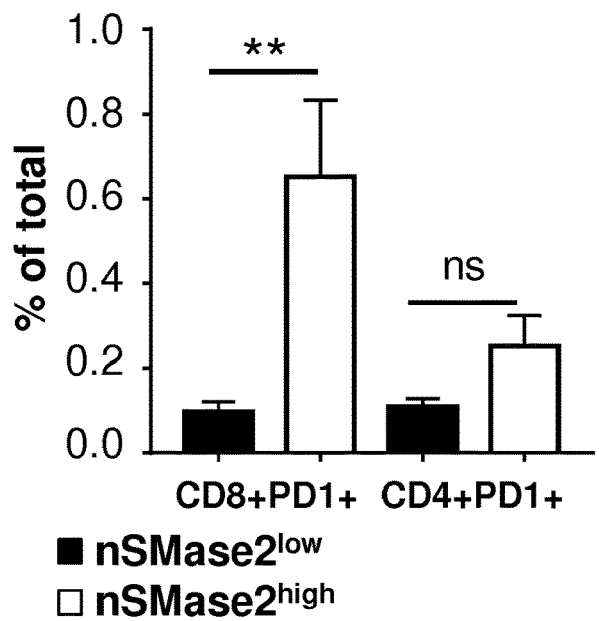
Figure 7B

METHODS AND PHARMACEUTICAL COMPOSITIONS FOR ENHANCING CD8+ T CELL-DEPENDENT IMMUNE RESPONSES IN SUBJECTS SUFFERING FROM CANCER

FIELD OF THE INVENTION

The present invention relates to methods and pharmaceutical compositions for enhancing CD8+ T cell-dependent immune responses in subjects suffering from cancer.

BACKGROUND OF THE INVENTION

Sphingolipids (SLs) act as bioactive molecules in various signaling pathways, modulating cell growth, differentiation, migration and death as well as cancer progression (1-4). Our group has recently documented some alterations of SL metabolism in cancer, including melanoma (5-8) and breast cancer (9). The expression and activity of several SL-metabolizing enzymes are indeed dysregulated in cancer, limiting the accumulation of the anti-oncometabolite ceramide, and, conversely, facilitating the accumulation of the oncometabolite sphingosine-1-phosphate (S1P) (5-9).

A growing body of evidence in the literature indicates that SL metabolites are critical regulators of melanoma progression. For instance, glycosphingolipid depletion impairs B16 melanoma growth both in vitro and in vivo (10). In addition, overexpression of the non-lysosomal glucocerebrosidase GBA2, which is frequently downregulated in human melanoma, triggers glucosylceramide breakdown to ceramide, leading to endoplasmic reticulum stress and subsequent apoptosis of melanoma cell lines (7). In sharp contrast, expression of acid ceramidase prevents ceramide accumulation and cell death induced by dacarbazine (6).

Ceramide can be generated by sphingomyelin (SM) hydrolysis, as a consequence of sphingomyelinase (SMase) activation (11, 12). Several SMases have been described so far including neutral, alkaline and acid SMases (13). Acid SMase deficiency is responsible for Niemann-Pick disease, a lysosomal storage disorder associated with SM accumulation (14). The growth of B16F1 melanoma cell line is increased in acid SMase-deficient mice, indicating that acid SMase-dependent SM-ceramide pathway plays some critical role in melanoma microenvironment (15), most likely by modulating tumor angiogenesis rather than the anti-melanoma immune response (16). Furthemore, acid SMase expression in human and mouse melanoma cells enhances the activation of the extracellular signal-regulated kinase (ERK), which phosphorylates the Microphthalmia-Associated Transcription Factor (MITF), leading to its proteasomal degradation (17). Consequently, acid SMase limits the expression of key proteins involved in melanoma progression, such as cdk2, Bcl-2 and cMet, which are under the control of MITF (17). More recently, melanoma acid SMase was shown to enhance the anti-melanoma immune response in mice (18).

Among the neutral SMases, neutral SMase 2, which is encoded by SMPD3 (19), is activated by diverse stimuli, including pro-inflammatory cytokines, such as IL-1β (20) and TNFα (21-23). Daunorubicin increased the transcription of SMPD3 in MCF-7 breast cancer cells, enhancing cell death (24). In addition, doxorubicin-induced MCF-7 cell growth arrest has been recently shown to involve an ATR/Chk1/p53-dependent SMPD3 transcription upregulation (25). Overexpression of nSMase 2 inhibits the growth of cancer cell lines, including MCF-7 (26) and F4328 mouse osteosarcoma (27) cell lines. Inactivating mutations have been found in SMPD3 gene in human acute myeloid and lymphoid leukemias (27). In addition, nSMase 2 is involved in exosome budding into multivesicular endosome (28). NSMase 2 expression in breast cancer cell lines enhances the secretion of exosomes, which contain the pro-angiogenic miR-210, facilitating tumor angiogenesis and metastasis (29), as well as the pro-motile miR-10b (30). NSMase 2 is also likely involved in cellular export of miRNAs to HDLs (31). To the best of our knowledge, the role of nSMase 2 in melanoma is currently unknown.

SLs are also critical modulators of immune response. For instance, some glycosphingolipids (ie., alphagalactosylceramide, iGb3) stimulate iNKT in a CD1d-dependent manner (32). S1P, through its ability to stimulate G protein-coupled S1P receptors, is involved in modulations of the lymphocyte trafficking and differentiation (33, 34). The immunosuppressive drug FTY720 (Fingolimod), a sphingosine analog, is phosphorylated by sphingosine kinases into FTY720-phosphate, which behaves as a functional antagonist of S1P receptors, leading to their internalization and degradation (35). Consequently, T lymphocytes, which remain sequestered into the thymus or lymph nodes, are less susceptible to trigger autoimmune diseases such as multiple sclerosis (36-38).

Despite findings pointing to the implication of the nSMase 2-dependent SM-ceramide pathway in inflammation, the biological function of nSMase 2 in adaptive immune response towards cancer cells remains unknown.

SUMMARY OF THE INVENTION

The present invention relates to methods and pharmaceutical compositions for enhancing CD8+ T cell-dependent immune responses in subjects suffering from cancer. In particular, the present invention is defined by the claims.

DETAILED DESCRIPTION OF THE INVENTION

Neutral sphingomyelinase 2 (nSMase 2), encoded by SMPD3, is weakly expressed in melanoma. Ectopic expression of nSMase 2 in B16K1 mouse melanoma cells failed to alter in vitro growth properties but dramatically reduced tumor growth in syngeneic wild-type (i.e., immunocompetent) mice. NSMase 2 overexpression elicits accumulation of both ceramide and CD8+ T lymphocytes in tumors. Importantly, nSMase 2 overexpression did not impair tumor growth in immunodeficient mice (i.e., nude and CD8-deficient mice), indicating that nSMase 2-mediated tumor growth inhibition involved a CD8+ T cell-dependent immune response. Sphingomyelinase enzyme activity was required for the above observations since overexpression of a catalytically inactive mutant of nSMase 2 had no effect on B16K1 tumor growth. NSMase 2 activity increased the immunogenicity of melanoma cell-derived exosomes, which were enriched in miR-155, a major pro-inflammatory miRNA. Interestingly, nSMase 2 overexpression in B16K1 cells greatly enhanced the therapeutic activity of immune checkpoint inhibitors (i.e., anti-CTLA-4 and anti-PD-1). Collectively, the data indicate that nSMase 2-triggered ceramide generation heightens exosome immunogenicity and tumor growth inhibition in experimental melanoma. Increasing intra-tumor ceramide content may serve as an original therapeutic strategy to enhance the immunogenicity of tumor cell-derived exosomes and stimulate anti-cancer immune response in melanoma.

Accordingly, a first object of the present invention relates to a method of enhancing the CD8+ T cell-dependent immune response in a subject suffering from cancer comprising administering to the subject a therapeutically effective amount of an agent capable of increasing intra-tumoral ceramide content.

A further object of the present invention relates to a method of treating cancer in a subject in need thereof comprising administering to the subject a therapeutically effective combination of an immune checkpoint inhibitor with an agent capable of increasing intra-tumoral ceramide content, wherein administration of the combination results in enhanced therapeutic efficacy relative to the administration of the immune checkpoint inhibitor alone.

As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma;

gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma;

retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the subject suffers from melanoma. As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found. 40-60% of melanomas carry an activating mutation in the gene encoding the serine-threonine protein kinase B-RAF (BRAF). Among the BRAF mutations observed in melanoma, over 90% are at codon 600, and among these, over 90% are a single nucleotide mutation resulting in substitution of glutamic acid for valine (BRAFV600E).

In some embodiments, the subject suffers from a melanoma resistant to BRAF inhibitors. As used herein, the term "resistant" refers to the repeated outbreak of melanoma, or a progression of the melanoma independently of whether the disease was cured before said outbreak or progression. As used herein, the term "BRAF inhibitor" refers to an agent that is capable of inhibiting BRAF kinase or mutated BRAF kinase activity (one or more mutated forms of serine-threonine protein kinase B-RAF (BRAF)) (e.g. BRAFV600E). Accordingly, the term "BRAF inhibitors" encompasses within its scope a compound that is capable of inhibiting BRAF or its mutated form; or a compound that is capable of inhibiting V600 mutated form of BRAF. Examples of BRAF inhibitors include but are not limited to BAY43-9006 (sorafenib, Bayer), vemurafenib (PLX4032, Plexxikon; RG7204, R05185426, Hofmann-LaRoche), GDC-0879 (GlaxoSmithKline), dabrafenib (GSK21 18436, GlaxoSmithKline), PLX4720 (Hofmann-LaRoche), BMS-908662 (XL281, Bristol-Myers Squibb), LGX818 (Novartis), PLX3603 (RO5212054, Hofmann-LaRoche), ARQ-736 (ArQule), DP-4978 (Deciphera) or RAF265 (Novartis).

In some embodiments, the subject suffers from a melanoma with elevated plasma lactate dehydrogenase (LDH). Plasma LDH can be considered "elevated" according to the method of the present invention if it exceeds plasma LDH levels typically found in a negative control, i.e., a healthy mammal of the same species. Typically, plasma LDH can be considered "elevated" if it exceeds about 212 IU/mL. Preferably, plasma LDH is considered "elevated" if it exceeds about 250 IU/mL. More preferably, plasma LDH is considered "elevated" if it exceeds about 287 IU/mL.

As used herein, the term "treatment" or "treat" refer to both prophylactic or preventive treatment as well as curative or disease modifying treatment, including treatment of patients at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the expression "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy. As used herein, the expression "relative to" when used in the context of comparing the activity and/or efficacy of a combination composition comprising the immune checkpoint inhibitor with the agent capable of increasing intra-tumoral ceramide content to the activity and/or efficacy of the immune checkpoint alone, refers to a comparison using amounts known to be comparable according to one of skill in the art.

In particular, the method of the present invention is particularly suitable for the treatment of cancer characterized by a low tumor infiltration of CD8+ T cells. Typically said tumor-infiltration of CD8+ T cells is determined by any convention method in the art. For example, said determination comprises quantifying the density of CD8+ T cells in a tumor sample obtained from the subject.

As used herein, the term "tumor tissue sample" means any tissue tumor sample derived from the patient. Said tissue sample is obtained for the purpose of the in vitro evaluation. In some embodiments, the tumor sample may result from the tumor resected from the patient. In some embodiments, the tumor sample may result from a biopsy performed in the primary tumor of the patient or performed in metastatic samples distant from the primary tumor of the patient. For example an endoscopical biopsy performed in the bowel of the patient affected by a colorectal cancer. In some embodiments, the tumor tissue sample encompasses (i) a global primary tumor (as a whole), (ii) a tissue sample from the center of the tumor, (iii) a tissue sample from the tissue directly surrounding the tumor which tissue may be more specifically named the "invasive margin" of the tumor, (iv) lymphoid islets in close proximity with the tumor, (v) the lymph nodes located at the closest proximity of the tumor, (vi) a tumor tissue sample collected prior surgery (for follow-up of patients after treatment for example), and (vii) a distant metastasis. As used herein the "invasive margin" has its general meaning in the art and refers to the cellular environment surrounding the tumor. In some embodiments, the tumor tissue sample, irrespective of whether it is derived from the center of the tumor, from the invasive margin of the tumor, or from the closest lymph nodes, encompasses pieces or slices of tissue that have been removed from the tumor center of from the invasive margin surrounding the tumor, including following a surgical tumor resection or following the collection of a tissue sample for biopsy, for further quantification of one or several biological markers, notably through histology or immunohistochemistry methods, through flow cytometry methods and through methods of genes or proteins expression analysis, including genomic and proteomic analysis. The tumor tissue sample can, of course, be subjected to a variety of well-known post-collection preparative and storage techniques (e.g., fixation, storage, freezing, etc.). The sample can be fresh, frozen, fixed (e.g., formalin fixed), or embedded (e.g., paraffin embedded).

In some embodiments, the quantification of density of CD8+ T cells is determined by immunohistochemistry (IHC). For example, the quantification of the density of CD8+ T cells is performed by contacting the tumor tissue sample with a binding partner (e.g. an antibody) specific for a cell surface marker of said cells. Typically, the quantification of density of CD8+ T cells is performed by contacting the tumor tissue sample with a binding partner (e.g. an antibody) specific for CD8. Typically, the density of CD8+ T cells is expressed as the number of these cells that are counted per one unit of surface area of tissue sample, e.g. as the number of cells that are counted per $cm^2$ or $mm^2$ of surface area of tumor tissue sample. In some embodiments, the density of cells may also be expressed as the number of cells per one volume unit of sample, e.g. as the number of cells per cm$^3$ of tumor tissue sample. In some embodiments, the density of cells may also consist of the percentage of the specific cells per total cells (set at 100%). Immunohistochemistry typically includes the following steps i) fixing the tumor tissue sample with formalin, ii) embedding said tumor tissue sample in paraffin, iii) cutting said tumor tissue sample into sections for staining, iv) incubating said sections with the binding partner specific for the marker, v) rinsing said sections, vi) incubating said sections with a secondary antibody typically biotinylated and vii) revealing the antigen-antibody complex typically with avidin-biotin-peroxidase complex. Accordingly, the tumor tissue sample is firstly incubated the binding partners. After washing, the labeled antibodies that are bound to marker of interest are revealed by the appropriate technique, depending of the kind of label is borne by the labeled antibody, e.g. radioactive, fluorescent or enzyme labels. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems. For example, one or more labels can be attached to the antibody, thereby permitting detection of the target protein (i.e the marker). Exemplary labels include radioactive isotopes, fluorophores, ligands, chemiluminescent agents, enzymes, and combinations thereof. In some embodiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. $^3$H, $^{14}$C, $^{32}$P, $^{35}$S or $^{125}$I) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In other examples, the antibody can be conjugated to peptides or proteins that can be detected via a labeled binding partner or antibody. In an indirect IHC assay, a secondary antibody or second binding partner is necessary to detect the binding of the first binding partner, as it is not labeled. The resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, scanning probe microscopes and imaging infrared detectors. In some examples, the image can be captured digitally. The obtained images can then be used for quantitatively or semi-quantitatively determining the amount of the marker in the sample. Various automated sample processing, scanning and analysis systems suitable for the use with immunohistochemistry are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549). The image can be quantitatively or semi-quantitatively analyzed and scored based on staining intensity of the sample. Quantitative or semi-quantitative histochemistry refers to method of scanning and scoring samples that have undergone histochemistry, to identify and quantitate the presence of the specified biomarker (i.e. the marker). Quantitative or semi-quantitative methods can employ imaging software to detect staining densities or amount of staining or methods of detecting staining by the human eye, where a trained operator ranks results numerically. For example, images can be quantitatively analyzed using a pixel count algorithms (e.g., Aperio Spectrum Software, Automated QUantitatative Analysis platform (AQUA® platform), and other standard methods that measure or quantitate or semi-quantitate the degree of staining; see e.g., U.S. Pat. Nos. 8,023,714; 7,257,268; 7,219,016; 7,646,905; published U.S. Patent Publication No. US20100136549 and 20110111435; Camp et al. (2002) Nature Medicine, 8:1323-1327; Bacus et al. (1997) Analyt Quant Cytol Histol, 19:316-328). A ratio of strong positive stain (such as brown stain) to the sum of total stained area can be calculated and scored. The amount of the detected biomarker (i.e. the marker) is quantified and given as a percentage of positive pixels and/or a score. For example, the amount can be quantified as a percentage of positive pixels. In some examples, the amount is quantified as the percentage of area stained, e.g., the percentage of positive pixels. For example, a sample can have at least or about at least or about 0, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 40%, 45%, 50%, 55%, 60%, 65%, 70%, 75%, 80%, 85%, 90%, 95% or more positive pixels as compared to the total staining area. In some embodiments, a score is given to the sample that is a numerical representation of the intensity or amount of the histochemical staining of the sample, and represents the amount of target biomarker (e.g., the marker) present in the sample. Optical density or percentage area values can be given a scaled score, for example on an integer scale. Thus, in some embodiments, the method of the present invention comprises the steps consisting in i)

providing one or more immunostained slices of tissue section obtained by an automated slide-staining system by using a binding partner capable of selectively interacting with the marker (e.g. an antibody as above described), ii) proceeding to digitalisation of the slides of step a. by high resolution scan capture, iii) detecting the slice of tissue section on the digital picture iv) providing a size reference grid with uniformly distributed units having a same surface, said grid being adapted to the size of the tissue section to be analyzed, and v) detecting, quantifying and measuring intensity of stained cells in each unit whereby the number or the density of cells stained of each unit is assessed.

In some embodiments, the cell density of CD8+ T cells is determined in the whole tumor tissue sample, is determined in the invasive margin or centre of the tumor tissue sample or is determined both in the centre and the invasive margin of the tumor tissue sample.

Accordingly a further object of the present invention relates to a method of treating cancer in a subject in need thereof comprising i) quantifying the density of CD8+ T cells in a tumor tissue sample obtained from the subject ii) comparing the density quantified at step i) with a predetermined reference value and iii) administering to the subject a therapeutically effective amount of an agent capable of increasing intra-tumoral ceramide content when the density quantified at step i) is lower than the predetermined reference value.

A further object of the present invention relates to a method of treating cancer in a subject in need thereof comprising i) quantifying the density of CD8+ T cells in a tumor tissue sample obtained from the subject ii) comparing the density quantified at step i) with a predetermined reference value and iii) administering to the subject a therapeutically effective combination of an immune checkpoint inhibitor with an agent capable of increasing intra-tumoral ceramide content when the density quantified at step i) is lower than the predetermined reference value.

Typically, the predetermined reference value correlates with the survival time of the subject. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they've become cancer-free (achieved remission). DSF gives more specific information and is the number of people with a particular cancer who achieve remission. Also, progression-free survival (PFS) rates (the number of people who still have cancer, but their disease does not progress) includes people who may have had some success with treatment, but the cancer has not disappeared completely. As used herein, the expression "short survival time" indicates that the patient will have a survival time that will be lower than the median (or mean) observed in the general population of patients suffering from said cancer. When the patient will have a short survival time, it is meant that the patient will have a "poor prognosis". Inversely, the expression "long survival time" indicates that the patient will have a survival time that will be higher than the median (or mean) observed in the general population of patients suffering from said cancer. When the patient will have a long survival time, it is meant that the patient will have a "good prognosis".

In some embodiments, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of cell densities in properly banked historical patient samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after quantifying the density of CD8+ T cells in a group of reference, one can use algorithmic analysis for the statistic treatment of the measured densities in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value is determined by carrying out a method comprising the steps of a) providing a collection of tumor tissue samples from subject suffering from the cancer of interest; b) providing, for each tumor tissue sample provided at step a), information relating to the actual clinical outcome for the corresponding patient (i.e. the duration of the disease-free survival (DFS) and/or the overall survival (OS)); c) providing a serial of arbitrary quantification values; d) quantifying the density of CD8+ T cells for each tumor tissue sample contained in the collection provided at step a); e) classifying said tumor tissue samples in two groups for one specific arbitrary quantification value provided at step c), respectively: (i) a first group comprising tumor tissue samples that exhibit a quantification value for level that is lower than the said arbitrary quantification value contained in the said serial of quantification values; (ii) a second group comprising tumor tissue samples that exhibit a quantification value for said level that is higher than the said arbitrary quantification value contained in the said serial of quantification values;

whereby two groups of tumor tissue samples are obtained for the said specific quantification value, wherein the tumor tissue samples of each group are separately enumerated; f) calculating the statistical significance between (i) the quantification value obtained at step e) and (ii) the actual clinical outcome of the patients from which tumor tissue samples contained in the first and second groups defined at step f) derive; g) reiterating steps f) and g) until every arbitrary quantification value provided at step d) is tested; h) setting the said predetermined reference value as consisting of the arbitrary quantification value for which the highest statistical significance (most significant) has been calculated at step g). For example the density of CD8+ T cells has been assessed for 100 tumor tissue samples of 100 patients. The 100 samples are ranked according to the density of CD8+ T cells. Sample 1 has the highest density and sample 100 has the lowest density. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the density of CD8+ T cells corresponding to the boundary between both subsets for which the p value is minimum is considered as the predetermined reference value. It should be noted that the predetermined reference value is not necessarily the median value of cell densities. Thus in some embodiments, the predetermined reference value thus allows discrimination between a poor and a good prognosis with respect to DFS and OS for a patient. Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the outcome can be determined by comparing the density of CD8+ T cells with the range of values which are identified. In some embodiments, a cut-off value thus consists of a range of quantification values, e.g. centered on the quantification value for which the highest statistical significance value is found (e.g. generally the minimum p value which is found).

A further object of the present invention relates to a method of enhancing the potency of an immune checkpoint inhibitor administered to a subject as part of a treatment regimen, the method comprising administering a pharmaceutically effective amount of an agent capable of increasing intra-tumoral ceramide content to a subject in combination with the immune checkpoint inhibitor.

As used herein the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because the tumor microenvironment has relatively high levels of adenosine, which lead to a negative immune feedback loop through the activation of A2AR. B7-H3, also called CD276, was originally understood to be a co-stimulatory molecule but is now regarded as co-inhibitory. B7-H4, also called VTCN1, is expressed by tumor cells and tumor-associated macrophages and plays a role in tumor escape. B and T Lymphocyte Attenuator (BTLA), also called CD272, is a ligand of HVEM (Herpesvirus Entry Mediator). Cell surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152 is overexpressed on Treg cells serves to control T cell proliferation. IDO, Indoleamine 2,3-dioxygenase, is a tryptophan catabolic enzyme, a related immune-inhibitory enzymes. Another important molecule is TDO, tryptophan 2,3-dioxygenase. IDO is known to suppress T and NK cells, generate and activate Tregs and myeloid-derived suppressor cells, and promote tumor angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tc1 function by triggering cell death upon interaction with its ligand, galectin-9. VISTA. Short for V-domain Ig suppressor of T cell activation, VISTA is primarily expressed on hematopoietic cells so that consistent expression of VISTA on leukocytes within tumors may allow VISTA blockade to be effective across a broad range of solid tumors.

As used herein, the term "immune checkpoint inhibitor" has its general meaning in the art and refers to any compound inhibiting the function of an immune inhibitory checkpoint protein. Inhibition includes reduction of function and full blockade. Preferred immune checkpoint inhibitors are antibodies that specifically recognize immune checkpoint proteins. A number of immune checkpoint inhibitors are known and in analogy of these known immune checkpoint protein inhibitors, alternative immune checkpoint inhibitors may be developed in the (near) future. The immune checkpoint inhibitors include peptides, antibodies, nucleic acid molecules and small molecules. In particular, the immune checkpoint inhibitor of the present invention is administered for enhancing the proliferation, migration, persistence and/or cytoxic activity of CD8+ T cells in the subject and in particular the tumor-infiltrating of CD8+ T cells of the subject. As used herein "CD8+ T cells" has its general meaning in the art and refers to a subset of T cells, which express CD8 on their surface. They are MHC class I-restricted, and function as cytotoxic T cells. "CD8+ T cells" are also called cytotoxic T lymphocytes (CTL), T-killer cells, cytolytic T cells, or killer T cells. CD8 antigens are members of the immunoglobulin supergene family and are associative recognition elements in major histocompatibility complex class I-restricted interactions. The ability of the immune checkpoint inhibitor to enhance T CD8 cell killing activity may be determined by any assay well known in the art. Typically said assay is an in vitro assay wherein CD8+ T cells are brought into contact with target cells (e.g. target cells that are recognized and/or lysed by CD8+ T cells). For example, the immune checkpoint inhibitor of the present invention can be selected for the ability to increase specific lysis by CD8+ T cells by more than about 20%, preferably with at least about 30%, at least about 40%, at least about 50%, or more of the specific lysis obtained at the same effector: target cell ratio with CD8+ T cells or CD8 T cell lines that are contacted by the immune checkpoint inhibitor of the present invention. Examples of protocols for classical cytotoxicity assays are conventional.

Thus the expression "enhancing the potency of an immune checkpoint" refers to the ability of the agent capable of increasing intra-tumoral ceramide content to increase the ability of the immune checkpoint inhibitor to enhance the proliferation, migration, persistence and/or cytoxic activity of CD8+ T cells.

In some embodiments, the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545, 807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the antibody comprises human heavy chain constant regions sequences but will not deplete CD8+ T cells to which they are bound and preferably do not comprise an Fc portion that induces antibody dependent cellular cytotoxicity (ADCC). As used herein, the term "depleting", with respect to CD8+ T cells means a process, method, or compound that can kill, eliminate, lyse or induce such killing, elimination or lysis, so as to negatively affect the number of CD8+ T cells present in a sample or in a subject. The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.). In some embodiments the antibody of the present invention does not lead, directly or indirectly, to the depletion of CD8+ T cells (e.g. do not lead to a 10%, 20%, 50%, 60% or greater elimination or decrease in number CD8+ T cells). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab') 2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4.

Examples of PD-1 and PD-L1 antibodies are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-1 (B7-H1) blockade.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94). As used herein, the term "TIM-3" has its general meaning in the art and refers to T cell immunoglobulin and mucin domain-containing molecule 3. The natural ligand of TIM-3 is galectin 9 (Gal9). Accordingly, the term "TIM-3 inhibitor" as used herein refers to a compound, substance or composition that can inhibit the function of TIM-3. For example, the inhibitor can inhibit the expression or activity of TIM-3, modulate or block the TIM-3 signaling pathway and/or block the binding of TIM-3 to galectin-9. Antibodies having specificity for TIM-3 are well known in the art and typically those described in WO2011155607, WO2013006490 and WO2010117057.

In some embodiments, the immune checkpoint inhibitor is an IDO inhibitor. Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. Preferably the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

In some embodiments, the agent capable of increasing intra-tumoral ceramide content refers to a neutral sphingomyelinase 2 (nSMase 2) polypeptide or a polynucleotide encoding for a neutral sphingomyelinase 2 (nSMase 2) polypeptide.

As used herein, the terms "nSMase2" has its general meaning in the art and refer to the human neutral sphingomyelinase 2 (nSMase 2). Exemplary amino acid sequences for nSMase2 is SEQ ID NO:1. Exemplary nucleic acid sequences for nSMase2 is SEQ ID NO: 2. The term also include nSMase2 variants include proteins substantially homologous to native nSMase2, i.e., proteins having one or more naturally or non-naturally occurring amino acid deletions, insertions or substitutions (e.g., nSMase2 derivatives, homologs and fragments).

```
                                       SEQ ID NO: 1
MVLYTTPFPN SCLSALHCVS WALIFPCYWL VDRLAASFIP

TTYEKRQRAD DPCCLQLLCT ALFTPIYLAL LVASLPFAFL

GFLFWSPLQS ARRPYIYSRL EDKGLAGGAA LLSEWKGTGP

GKSFCFATAN VCLLPDSLAR VNNLFNTQAR AKEIGQRIRN

GAARPQIKIY IDSPTNTSIS AASFSSLVSP QGGDGVARAV

PGSIKRTASV EYKGDGGRHP GDEAANGPAS GDPVDSSSPE

DACIVRIGGE EGGRPPEADD PVPGGQARNG AGGGPRGQTP

NHNQQDGDSG SLGSPSASRE SLVKGRAGPD TSASGEPGAN

SKLLYKASVV KKAAARRRRH PDEAFDHEVS AFFPANLDFL

CLQEVFDKRA ATKLKEQLHG YFEYILYDVG VYGCQGCCSF

KCLNSGLLFA SRYPIMDVAY HCYPNKCNDD ALASKGALFL

KVQVGSTPQD QRIVGYIACT HLHAPQEDSA IRCGQLDLLQ

DWLADFRKST SSSSAANPEE LVAFDVVCGD FNFDNCSSDD

KLEQQHSLFT HYRDPCRLGP GEEKPWAIGT LLDTNGLYDE
```

-continued
DVCTPDNLQK VLESEEGRRE YLAFPTSKSS GQKGRKELLK

GNGRRIDYML HAEEGLCPDW KAEVEEFSFI TQLSGLTDHL

PVAMRLMVSS GEEEA

SEQ ID NO: 2
ATGGTTTTGTACACGACCCCCTTTCCTAACAGCTGTCTGTCCGCCCTGCA

CTGTGTGTCCTGGGCCCTTATCTTTCCATGCTACTGGCTGGTGGACCGGC

TCGCTGCCTCCTTCATACCCACCACCTACGAGAAGCGCCAGCGGGCAGAC

GACCCGTGCTGCCTGCAGCTGCTCTGCACTGCCCTCTTCACGCCCATCTA

CCTGGCCCTCCTGGTGGCCTCGCTGCCCTTTGCGTTTCTCGGCTTTCTCT

TCTGGTCCCCACTGCAGTCGGCCCGCCGGCCCTACATCTATTCACGGCTG

GAAGACAAGGGCCTGGCCGGTGGGGCAGCCCTGCTCAGTGAATGGAAGGG

CACGGGGCCTGGCAAAAGCTTCTGCTTTGCCACTGCCAACGTCTGCCTCC

TGCCCGACTCACTCGCCAGGGTCAACAACCTTTTTAACACCCAAGCGCGG

GCCAAGGAGATCGGGCAGAGAATCCGCAATGGGGCCGCCCGGCCCCAGAT

CAAAATTTACATCGACTCCCCCACCAATACCTCCATCAGCGCCGCTAGCT

TCAGCAGCCTGGTGTCACCACAGGGCGGCGATGGGGTGGCCCGGGCCGTC

CCCGGGAGCATTAAGAGGACAGCCTCTGTGGAGTACAAGGGTGACGGTGG

GCGGCACCCCGGTGACGAGGCTGCCAACGGCCCAGCCTCTGGGGACCCTG

TCGACAGCAGCAGCCCGGAGGATGCCTGCATCGTGCGCATCGGTGGCGAG

GAGGGCGGCCGGCCACCTGAAGCTGACGACCCTGTGCCTGGGGGCCAGGC

CAGGAACGGAGCTGGCGGGGGCCCAAGGGGCCAGACGCCCAACCATAATC

AGCAGGACGGGGATTCAGGGAGCCTGGGCAGCCCCTCGGCCTCCCGGGAG

TCCCTGGTGAAGGGGCGAGCTGGGCCAGACACCAGTGCCAGCGGGGAGCC

AGGTGCCAACAGCAAGCTCCTGTACAAGGCCTCGGTGGTGAAGAAGGCGG

CTGCACGCAGGAGGCGGCACCCCGACGAGGCCTTCGACCATGAGGTCTCC

GCCTTCTTCCCCGCCAACCTGGACTTCCTGTGCCTGCAGGAGGTGTTTGA

CAAGCGAGCAGCCACCAAATTGAAAGAGCAGCTGCACGGCTACTTCGAGT

ACATCCTGTACGACGTCGGGGTCTACGGCTGCCAGGGCTGCTGCAGCTTC

AAGTGTCTCAACAGCGGCCTCCTCTTTGCCAGCCGCTACCCCATCATGGA

CGTGGCCTATCACTGTTACCCCAACAAGTGTAACGACGATGCCCTGGCCT

CTAAGGGAGCTCTGTTTCTCAAGGTGCAGGTGGGAAGCACACCTCAGGAC

CAAAGAATCGTCGGGTACATCGCCTGCACACACCTGCATGCCCCGCAAGA

GGACAGCGCCATCCGGTGTGGGCAGCTGGACCTGCTTCAGGACTGGCTGG

CTGATTTCCGAAAATCTACCTCCTCGTCCAGCGCAGCCAACCCCGAGGAG

CTGGTGGCATTTGACGTCGTCTGTGGAGATTTCAACTTTGATAACTGCTC

CTCTGACGACAAGCTGGAGCAGCAACACTCCCTGTTCACCCACTACAGGG

ACCCCTGCCGCCTGGGGCCTGGTGAGGAGAAGCCGTGGGCCATCGGTACT

CTGCTGGACACGAACGGCCTGTACGATGAGGATGTGTGCACCCCCGACAA

CCTGCAGAAGGTCCTGGAGAGTGAGGAGGGCCGCAGGGAGTACCTGGCGT

TTCCCACCAGCAAGAGCTCGGGCCAGAAGGGGCGGAAGGAGCTGCTGAAG

GGCAACGGCCGGCGCATCGACTACATGCTGCATGCAGAGGAGGGGCTGTG

-continued
CCCAGACTGGAAGGCCGAGGTGGAAGAATTCAGTTTTATCACCCAGCTGT

CCGGCCTGACGGACCACCTGCCAGTAGCCATGCGACTGATGGTGTCTTCG

GGGGAGGAGGAGGCATAG

In some embodiments, the nSMase 2 polypeptide refers to a polypeptide comprising an amino acid sequence of a nSMase2 variant can be at least 90% of identity with SEQ ID NO:1.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

Typically, the polynucleotide encoding for nSMase2 is delivered with a vector. In its broadest sense, a "vector" is any vehicle capable of facilitating the transfer of the antisense oligonucleotide siRNA or ribozyme nucleic acid to the cells. Preferably, the vector transports the polynucleotide to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the polynucleotide sequence of interest. Viral vectors are a preferred type of vector and include, but are not limited to polynucleotide sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol.7, Humana Press, Inc., Clifftton, N.J., 1991). Preferred viruses for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion. Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA.

Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In some embodiments, the agent is able to increase the endogenous nSMase 2 expression level in the tumoral cells. In some embodiments, the agent is selected from the group consisiting of DNA methyltransferase inhibitors and histone deacetylase inhibitors.

As used herein, the term "DNA methyltransferase inhibitor" or "DNMTi" has its general meaning in the art refers to an agent that inhibits the transfer of a methyl group to DNA. Examples of small molecule inhibitors of histone methyltransferases are described below. Such inhibitors can target both lysine and arginine methyltransferases, for example, those disclosed in WO 2013/063417 (the contents of which are hereby incorporated by reference in its entirety). S-adenosyl-methionine (SAM) analog inhibitors are broadly inhibiting to methyltransferases, as they are analogs of the methyl substrate, and therefore competitively inhibit methyltransferases. Examples of SAM analogs include, but are not limited to EPZ004777 (CAS 1338466-77-5; BioVision Incoporated). Small molecule inhibitors of lysine histone methyltransferases include BTX 01294 (also known as 2-(Hexahydro-4-methyl-1H-1,4-diazepin-1-yl)-6,7-dimethoxy-N-[1-(phenylmethyl)-4-piperidinyl]-4-quinazolinamine trihydrochloride hydrate; Tocris Biosciences)) (and its derivative TM2-115), 3-Deazaneplanocin A hydrochloride (DZnep) (Tocris Biosciences), chaetocin (CAS 28094-03-2; Tocris Biosciences; Sigma-Aldrich), SGC 0946 (Tocris Biosciences, Selleck Chemicals), UNC 0224 (CAS 1197196-48-7; Tocris Biosciences, Cayman Chemical), UNC 0638 (CAS 1255517-77-1; Tocris Bioscience), UNC 0646 (CAS 1320288-17-2; Tocris Biosciences), 2-cyclohexyl-N-(1-isopropylpiperidin-4-yl)-6-methoxy-7-(3-(pyrrolidin-1-yl)propoxy) quinazolin-4-amine, polyhydroxy derivatives of (2,3,7,8-tetrahydroxy[1] benzopyrano (5 4,3 (de)Mbenzopyran5, 10-dione) (for example, those disclosed in WO2008/001391). Inhibitors of Ezh2 include S-adenosyl-L-homocysteine and analogs or derivatives thereof (for example, those disclosed in WO20.12/034132; hereby i co oraiεd by reference in its entirety), BIX-01294 (trihydrochloride hydrate) (2-(Hexahydro-4-methyl-1H-1,4-diazepin-1-yl)-6,7-dimethoxy-N-[1-(phenylmethyl)-4-piperidinyl]-4-quinazolinamine trihydrochloride; Tocris Biosciences) is a diazepin-quinazolinamine derivative. This inhibitor is a lysine methyltransferase inhibitor, and does not compete with cofactor S-adenosyl-methionine. Specifically, BIX-01294 has been shown to inhibit methylation at lysine 9 of histone H3 (H3K9). Reported activity includes inhibition of dimethylation of H3K9 (H3K9me2), and inhibition of G9a-like protein and G9a histone lysine methyltransferase. Examples of polynucleotides that inhibit histone methyltransferase activity and/or expression include RNA-interfering polynucleotides. For example, siRNAs that specifically bind and target any of the histone methyltransferases disclosed herein, preferably Setdb2, Setd7, Setd8, Prmt7, Ezh1, Ezh2, or Aurkb, for degradation, thereby inhibiting expression or function of the methyltransferase. siRNAs are commercially available and custom designed, synthesized, and purchased, for example, from Dharmacon, Inc. Alternatively, short hairpin RNA (shRNA) sequences can be designed by the skilled artisan using art-recognized techniques and the nucleotide sequences of the methyltransferases disclosed herein.

As used herein, the term "histone deacetylase inhibitor" and "HDACi" has its general meaning in the art and refers to a compound, which is capable of interacting with a histone deacetylase and inhibiting its activity. Examples thereof include, but are not limited to, a hydroxamic acid derivative, a cyclic tetrapeptide, a short-chain fatty acid (SCFA) derivative, a benzamide derivative, an electrophilic ketone derivative, and other HDAC inhibitors. Examples of a hydroxamic acid derivative include, but are not limited to: suberoylanilide hydroxamic acid (SAHA) (Richon et al., Proc. Natl. Acad. Sci. U.S.A. 95, 3003-3007 (1998)); m-carboxy cinnamic acid bishydroxamide (CBHA) (Richon et al., supra); pyroxamide; trichostatin analogues such as trichostatin A (TSA) and trichostatin C (oghe et al., Biochem. Pharmacol. 56: 1359-1364 (1998)); salicylohydroxamic acid (Andrews et al., International J. Parasitology 30, 761-768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); 6-(3-chloiOphenylureido)car/>o/c hydroxamic acid (3C1-UCHA); oxamflatin [(2E)-5-[3-[(phenylsulfonyl)aminophenyl]-pent-2-en-4-ynohydroxamic acid] (Kim et al., Oncogene, 18: 2461-2470 (1999)); A-161906, Scriptaid (Su et al., Cancer Research, 60: 3137-3142(2000)); PXD-1O1(Prolifix); LAQ-824; CHAP; MW2796 (Andrews et al., supra); MW2996 (Andrews et al., supra); and any hydroxamic acid disclosed in U.S. Pat. Nos. 5,369,108, 5,932,616, 5,700,811, 6,087,367, and 6,511,990.

In some embodiments, the agent capable of increasing intra-tumoral ceramide content refers to a carrier that is suitable to deliver an amount of ceramide intra-tumorally.

As used herein a "ceramide" is any N-acylsphingosine. Ceramides include sphingo lipids in which the sphingosine is acylated with a fatty acid acyl-Co A derivative to form an N-acylsphingosine. Ceramide may be either naturally occurring or chemically synthesized.

In some embodiments, the carrier is a liposome. Examples of formulations of liposomes and other particulate carriers, particularly where ceramide is included are described in examples herein and in U.S. Patent Application Publication No. 2005/0025820. Further examples are described in Stover T et al, J Pharmacol Exp Ther., 2003, 307:468-475; and Stover T C, et al, Clin Cancer Res., 2005, 11:3465-3474. Liposomes used in methods according to the present invention typically have particle sizes in the range of about 1 nanometer to about 1 micron, inclusive, in diameter. Nano-sized liposomes having particle sizes in the range of about 1-100 nanometers, inclusive, in diameter are preferred. In embodiments in which a liposome nanocarrier is used, the liposome has a lipid-containing wall defining an internal volume. Further particulate carriers include other nanocarriers suitable for delivering the ceramide include but are not limited to nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further description of nanocarriers may be found in S. M. Moghimi et al, Nanomedicine: current status and future prospects, FASEB J. 2005, 19, 311-30.

As used herein the term "co-administering" means a process whereby the combination of the agent capable of increasing intra-tumoral ceramide content and the immune checkpoint inhibitor, is administered to the same patient. The agent capable of increasing intra-tumoral ceramide content and the immune checkpoint inhibitor may be administered simultaneously, at essentially the same time, or sequentially. If administration takes place sequentially, the agent capable of increasing intra-tumoral ceramide content is administered before the immune checkpoint inhibitor. The agent capable of increasing intra-tumoral ceramide content and the immune checkpoint inhibitor need not be administered by means of the same vehicle. The agent capable of increasing intra-tumoral ceramide content and the immune checkpoint inhibitor may be administered one or more times and the number of administrations of each component of the combination may be the same or different. In addition, the agent capable of increasing intra-tumoral ceramide content and the immune checkpoint inhibitor need not be administered at the same site.

As used herein, the term "therapeutically effective combination" as used herein refers to an amount or dose of an agent capable of increasing intra-tumoral ceramide content together with the amount or dose of the immune checkpoint inhibitor that is sufficient to treat the disease (e.g. cancer). The amount of the agent capable of increasing intra-tumoral ceramide content in a given therapeutically effective combination may be different for different individuals and different tumor types, and will be dependent upon the one or more additional agents or treatments included in the combination. The "therapeutically effective amount" is determined using procedures routinely employed by those of skill in the art such that an "improved therapeutic outcome" results. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the agent capable of increasing intra-tumoral ceramide content and the immune checkpoint inhibitor are administered to the subject in the form of a pharmaceutical composition. Typically, the agent capable of increasing intra-tumoral ceramide content and the immune checkpoint inhibitor may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The agent capable of increasing intra-tumoral ceramide content and the immune checkpoint inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: nSMase 2 over-expression in B16K1 cells does not alter cell growth in vitro.

A, B16K1 cells expressing (2+) or not (2−) V5-tagged nSMase 2 were analyzed by Western blot using anti-V5 and anti-β-actin antibodies. B, Neutral SMase activity in B16K1 nSMase 2+ (2+) and nSMase 2− (2−) as well as in mock-transfected B16K1 cells. C, Intracellular ceramide levels in B16K1 nSMase 2+(2+) and nSMase 2− (2−) as well as in mock-tranfected B16K1 cells. Data are expressed as the % of values obtained with mock-transfected B16K1 cells. Values are shown as means±sem of 3 independent experiments (B and C). D, In vitro B16K1 cell growth was evaluated in 10% FCS medium (left panel) or 0% FCS medium (left panel). Data are displayed as means±sem of triplicates from one representative experiment out of three. E, B16K1 cells were stably transduced with a control retroviral vector (B16K1 mock), a retroviral vector encoding WT (nSMase2 WT) or a catalytically inactive (nSMase2 C.I.) VS-tagged nSMase 2. Cells were analysed by Western blot using anti-V5 and anti-β-actin antibodies. F, Neutral SMase activity in B16K1 transduced with a control retroviral vector (B16K1 mock), a retroviral vector encoding WT (nSMase2 WT) or a catalytically inactive nSMase 2 (nSMase2 C.I.). Data are shown as means±sem of 3 independent experiments. (*: $p<0.05$; **: $p<0.01$). G, B16K1 melanoma cells were incubated or not with 1 μM of 5 aza-2 deoxycitidine (5-aza) during 72 hours or with 0.1 μM Trichostatine A (TSA) during the last 16 hours. Smpd3 expression was analysed by RT-qPCR. Data are shown as means±sem of 3 independent experiments.

Figure 2:
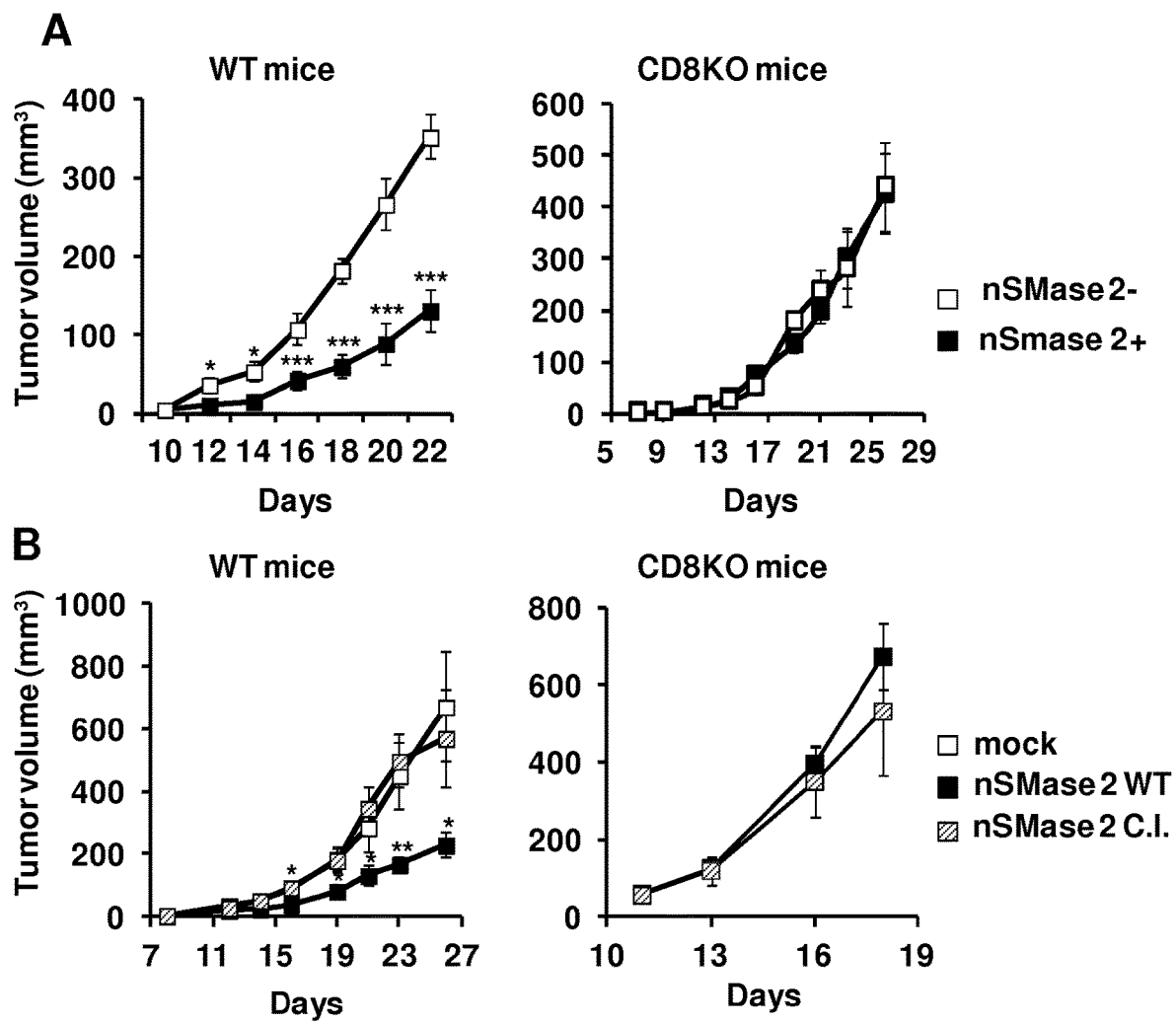

FIG. 2: Impact of nSMase 2 over-expression on B16K1 tumor growth in mice.

A, WT (left panel) or CD8 KO (right panel) mice were intradermally and bilaterally injected with $3\times10^5$ B16K1 nSMase 2+ (2+) or nSMase 2− (2−) cells. Tumor volume was determined at the indicated days with a calliper. Data are shown as means±sem of a minimum of 6 tumors per group (*: $p<0.05$; ***: $p<0.001$). B, B16K1 cells expressing or not (mock) a WT or catalytically inactive (C.I.) nSMase2 were intradermally and bilaterally injected in WT (left panel) or CD8 KO (right panel) mice and tumor volumes were determined at the indicated days. Data are displayed as means±sem of 8 tumors in CD8 KO and WT mice per group (*: $p<0.05$; **: $p<0.01$).

FIG. 3: Analysis of TILs and cytokines mRNA in B16K1 tumors over-expressing nSMase 2.

One million B16K1 cells transduced with a retroviral vector encoding a wild-type (WT) or catalytically inactive (C.I.) nSMase2 were intra-dermally injected in wild-type mice and 12 days later, tumors were collected. A, Tumors were weighed. B, In some experiments, tumors were dissociated and the tumor TIL content was analysed by flow cytometry. The proportion of total CD4+ (left panel) and CD8+ (right panel) TIL was determined. Data are shown as means±sem of 18 tumors per group. C, CD8+ T cells specific for Trp2 peptides were quantified using the dextramer technology. Representative staining (left panel) and proportion of total Trp2-specific CD8+ T cells are depicted. Data are shown as means±sem of 6 tumors per group. D, In additional experiments, RNA from tumors were purified and CXCL9 and IFNγ transcripts were analysed by RT-qPCR. Data are shown as means±sem of 8 determinations per group. (*: $p<0.05$; **: $p<0.01$).

FIG. 4: nSMase 2 enzyme activity enhances exosome immunogenicity.

Exosomes from B16K1 cells transduced with a retroviral vector encoding a wild-type (WT) or catalytically inactive (C.I.) nSMase2 were purified by ultracentifugation. A, Exosome preparation was observed by electronic microscopy. B, RNA was purified from exosomes produced by B16K1 cells expressing WT or C.I nSMase2 and the presence of miR-155 and miR-21a was analysed by RT-qPCR. Data are shown as means±sem of 4 independent experiments carried out with 4 independent exosome preparations. C, Bone marrow-derived dendritic cells were incubated with 10 μg/mL exosomes from B16K1 expressing WT or C.I nSMase2. After 24 h of co-culture, CXCL9, IL-12 and SOCS1 transcripts were analyzed by RT-qPCR. Data are displayed as means±sem of 3 independent experiments carried out with 2-3 independent exosome preparations. D, WT mice were intradermally co-injected with B16K1 cells and exosomes purified from B16K1 expressing WT or C.I nSMase2. 12 days after B16K1 inoculation, tumor volumes were measured at the indicated days with a calliper (left panel). The proportion of total CD8+ TIL was determined by flow cytometry (right panel). Data are shown as means±sem of 9 to 15 mice per group. (*: $p<0.05$; **: $p<0.01$).

Figure 5:
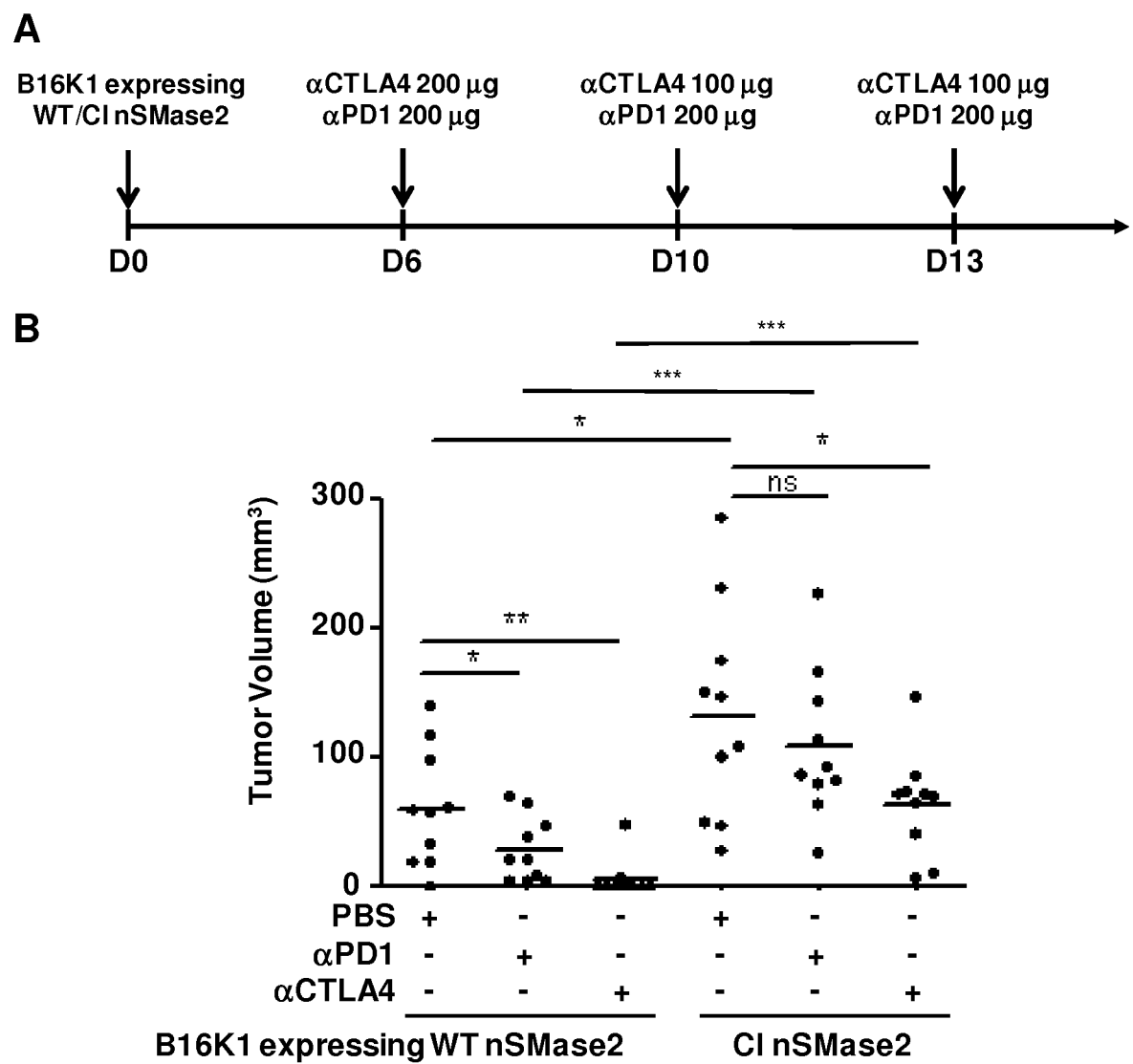

FIG. 5: nSMase2 enhances the response to immunotherapies.

WT mice were intradermally and bilaterally injected with $3\times10^5$ B16K1 melanoma cells expressing or not the wild type (WT) or catalytically inactive (C.I) nSMase2. Mice received intraperitoneal injection of anti-PD-1 antibodies (αPD-1, 200 μg) or anti-CTLA-4 antibodies (αCTLA-4, 200 μg for the first injection and then 100 μg) or vehicle (PBS) at days 6, 10 and 13 (n=10 tumors per group). A, Diagram representing the experimental protocol. B, Tumor volumes were measured using a calliper at day 17. (*: $p<0.05$; : $p<0.01$; *: $p<0.001$).

FIG. 6: Melanoma nSMase2 enhances CD8+ T cell-dependent immune responses. A, Analysis of overall survival in metastatic melanoma patients from the TCGA melanoma cohort, exhibiting high (80th percentile) and low (20th percentile) SMPD3 expression in melanoma samples. B, Heatmap for a selected list of genes in samples with highest ($SMPD3^{high}$) and lowest ($SMPD3^{low}$) SMPD3 expression. Genes were clustered using a Euclidean distant matrix and average linkage clustering. C, Correlation analyses of SMPD3 expression with the indicated genes. D-E, WT mice injected with B16K1 $nSMase2^{low}$ (black bars) or $nSMase2^{high}$ (white bars) were sacrificed and tumor-infiltrating leukocytes were analysed by flow cytometry (D). Alternatively, the levels of total (left panel) and specific subtypes (right panel) of ceramide were determined in tumors (E). (*: $p<0.05$; ***: $p<0.001$).

FIG. 7: Melanoma nSMase2 enhances the response to immunotherapies. A, Upper panel, heatmap for a selected list of genes in human metastatic melanoma samples exhibiting the highest ($SMPD3^{high}$) and lowest ($SMPD3^{low}$) SMPD3 expression. Genes were clustered using a Euclidean distant matrix and average linkage clustering. Lower panel, correlation analysis of SMPD3 and PDCD1 expression. B-D, WT mice were intradermally injected with B16K1 cells expressing high ($nSMase2^{high}$) or low ($nSMase2^{low}$) levels of nSMase2. At Day 12, tumors were collected, dissociated and the content of PD-1+CD8+ TILs was analysed by flow cytometry (B). Alternatively, mice received intraperitoneal injection of anti-PD-1 (αPD-1, 200 μg) or vehicle (PBS) at days 6, 10 and 13 (n=10 tumors per group). Individual tumor curves are depicted. Inserts, numbers indicate the number of total regression(s) out of total number of tumors (C). Overall survival was determined for each group (D) (*: $p<0.05$; : $p<0.01$; *: $p<0.001$).

EXAMPLES

Example 1

Material & Methods

Cells: B16K1 is a genetically modified cell line obtained from B16F10 cells, which stably express the MHC-I molecule H-2Kb (41-43). Cells were cultured in DMEM medium containing 10% heat-inactivated fetal calf serum (FCS). To study cell proliferation, B16K1 cells overexpressing or not WT VS-tagged nSMase 2 were cultured in DMEM medium containing 0 or 10% FCS. Cells were counted at the indicated times by using a cell counter (Beckman coulter).

For dendritic cell (DC) preparation, bone morrow derived cells were cultured in complete RPMI medium supplemented with 10% fetal bovine serum, penicillin, streptomycin, 50 µM β-mercaptoethanol and 20 ng/mL granulocyte macrophage colony-stimulating factor (GM-CSF) at 37° C. with 5% CO2. Medium was changed every 2-3 days. After at least 7 days of culture, DC differentiation was analyzed by FACS. In some experiments, DCs were cultured during 24 h with 10 µg/mL of exosomes.

B16K1 cell transfection: B16K1 cells were transfected (Superfect reagent, Qiagen) with a plasmid (pEF6-V5-TOPO) containing the cDNA encoding the mouse nSMase 2. Transfected cells were selected for their resistance to blasticidin (7 µg/mL) and subjected to limit dilution. Resistant cells were cultured in DMEM containing 7 µg/mL blasticidin and analysed by Western blot. Two cell populations were selected for the present study: B16K1 nSMase2+ and B16K1 nSMase2−, which overexpressed or not the VS-tagged nSMase 2, respectively. Mock-transfected B16K1 cells have been obtained by transfecting a plasmid conferring resistance to blasticidin.

Cloning of the His-nSMase2 WT and catalytically-inactive (D428A) in pMSCV-Puro: Retroviral expression vectors encoding wild-type (WT) or the mutant mouse nSMase-2 were obtained by cloning the product of the partial BamHI and PmeI digestion of pEF6-V5-His donor expression vectors encoding a WT or a catalytically inactive (D428A) mouse nSMase-2 into pMSCV-Puro (44) linearized with BglII and HpaI.

Retrovirus production and cell transduction: The generation of viruses has been described previously (45). Viral particles of WT and catalytically inactive (D428A) nSMase-2 derived from pMSCV-Puro vectors were produced to transduce 1 to $3 \times 10^6$ mouse B16K1 cells for 16 h in 6-well plates in the presence of Polybrene (8 µg/ml). Cells were then washed in phosphate-buffered saline (PBS), harvested, plated in complete medium containing puromycin (2.5 µg/ml) and incubated for 3 days before amplification and subsequent analysis of the polyclonal populations.

Mice: WT C57BL/6 mice were from Janvier laboratories. CD8-deficient C57BL/6 mice were a gift from Prof. J. van Meerwijk (INSERM U1043, Toulouse, France). Mice were housed in temperature-controlled rooms in the specific pathogen-free animal facility (Anexplo platform, Toulouse, France), kept on a 12-h light/dark cycle, and had unrestricted access to food and water. All animal studies were conducted according to national and international policies and were approved by the local committee for animal experimentation.

In vivo tumorigenesis: $3 \times 10^5$ B16K1 cells overexpressing or not the WT or catalytically-inactive V5-tagged nSMase 2 were intra-dermally injected in WT and CD8$^{-/-}$ mice. In some experiments, 1 µg of exosomes purified from B16K1 cells overexpressing the WT or catalytically-inactive nSMase 2 were co-injected with $3 \times 10^5$ parental B16K1 cells. Tumor volumes were measured using a caliper at the indicated days.

Immunotherapy protocol: $3 \times 10^5$ B16K1 cells were intra-dermally and bilaterally injected in wild-type mice (n=5 mice per condition). Mice received intraperitoneal injections of anti-PD-1 antibodies (αaPD-1, 200 µg) or anti-CTLA-4 antibodies (αCTLA-4, 200 µg for the first injection and then 100 µg) or vehicle (PBS) at days 6, 10 and 13. Tumor volumes were measured using a caliper at the indicated days.

Analysis of lymphocyte content in tumors: One million B16K1 cells overexpressing or not the WT or catalytically-inactive VS-tagged nSMase 2 were intra-dermally injected in WT mice. In some experiments, 3.3 µg exosomes purified from B16K1 cells overexpressing the WT or catalytically-inactive nSMase 2 were co-injected with $1 \times 10^6$ parental B16K1 cells. At day 12, mice were sacrificed and tumors were collected and digested with the Tumor Dissociation Kit, mouse (miltenyi). Cells were stained with the antibodies or MHC-I dextramers and live-dead reagent (Invitrogen) before flow cytometry analysis. Antibodies used in this study were anti-mouse CD45 (BD Biosciences, BUV395), anti-mouse Thy1 (Biolegend, APC-Cy7), anti-mouse CD8 (BD Biosciences, BV605) and anti-mouse CD4 (eBioscience, FITC).

Sphingomyelin analysis from B16K1 cell lines: $3 \times 10^6$ B16K1 cells were incubated in the presence of 1 µCi/mL [$^3$H]choline for 48 h. Cells were collected and sedimented at 4° C. by low-speed centrifugation, and cell pellets were immediately frozen at −20° C. Cell pellets were suspended in 0.6 mL of distilled water, and disrupted at 4° C. by brief sonication. Lipids were extracted, and [$^3$H]choline-labeled SM was quantified as previously reported (46).

Sphingolipid analysis from tumors: Tumors were collected and disrupted using the FastPREP technology (MP Biomedicals). Lipids were extracted from 5 mg of tumor samples. SM levels were quantified by measuring the lipid phosphorus content (47). Ceramide mass was measured essentially as described (48), using recombinant *Escherichia coli* diacylglycerol kinase (Calbiochem, Meudon, France) and [γ-32P]ATP. Radioactive ceramide-1-phosphate was isolated by TLC using chloroform/acetone/methanol/acetic acid/water (50:20:15:10:5, by volume) as developing solvent. Alternatively, SLs were measured by mass spectrometry on a Thermo Finnigan TSQ 7000 triple quadrupole mass spectrometer operating in a multiple reaction monitoring positive ionization mode as described previously (49). Results from mass spectrometry analysis were normalized to total protein concentration as determined using a Bradford assay.

Neutral sphingomyelinase activity measurement: Cellular and tumor nSMase activities were assayed as described previously (50) using [choline-methyl-$^{14}$C]SM (100,000 dpm/assay) as substrate.

Western blot analysis: Cells were washed and harvested in PBS containing 20 mM NaF, 20 mM sodium pyrophosphate, 1 mM NaVO$_4$, and 5 mM EDTA. Cells were lysed in a buffer containing 50 mM HEPES, pH 7.5, 150 mM NaCl, 10% glycerol, 1% Triton X-100, 0.5% deoxycholate, 1 mM NaVO$_4$, 10 mM β-glycerophosphate, 50 mM NaF, 1 mM phenylmethylsulfonyl fluoride, 10 µg/ml leupeptin, 2 µg/ml pepstatin A, and 10 µg/ml aprotinin, for 30 min on ice. Equal amounts of proteins were separated in a 7.5% SDS-polyacrylamide gel and blotted onto nitrocellulose membranes (Hybond-C, Amersham Pharmacia Biotech). Proteins were detected using anti-V5 and anti-actin antibody and an ECL detection system (Amersham Pharmacia Biotech).

Confocal microscopy analysis: B16K1 cells were cultured on glass coverslips for 24 h and fixed in PBS-paraformaldehyde. After permeabilization with saposin, cells were stained with anti-giantin and anti-V5 (Invitrogen) antibodies and dye-coupled secondary antibodies and analysed by confocal microscopy (Zeiss, LSM510).

Exosome purification. Cells were cultured in medium with exosome-free FCS, which was prepared by centrifugations to remove existing exosomes. Cell culture medium was collected after 5 days of culture and exosomes were isolated by differential centrifugations. Briefly, the culture medium was centrifuged at 10,000×g for 45 min. The supernatant was then centrifuged at 110,000×g for 70 min at 4° C. to pellet exosomes. Exosome pellet was then washed with PBS, and further centrifuged at 110,000×g for 70 min at 4° C. The resulting pellet was resuspended in PBS.

RNA isolation and qRT-PCR. RNA isolation from cells and exosomes was performed by using the Qiagen RNeasy mini kit and Qiagen miRNeasy kit respectively, according to manufacturer's instructions. Mature miRNA cDNA was made with a miRCURY LNA universal RT miRNA PCR kit using 20 ng of RNA from each sample (Exiqon). qPCR of mature miRNA was performed with the miRCURY LNA universal RT miRNA PCR kit SYBR green master mix with LNA primers for mmu-miR155-5p, mmumiR-21a-5p, miR-146-5p, RNU1A1 and 5S RNA (Exiqon). RNU1A1 and 5S RNA were used to normalize expression. cDNA from total RNA was made with SuperScript II Reverse Transcriptase by using 1 μg of RNA from each sample (Thermofischer). qPCR was performed with SYBR Green Master Mix (Takara) and primers for transcript encoding murine β-actin, HPRT, CXCL9, IFNγ, IL-12 and SOCS1 (Qiagen). For RNA isolation from tumors, one million B16K1 cells overexpressing WT or catalytically-inactive V5-tagged nSMase 2 were intra-dermally injected in WT mice. At day 12, mice were sacrificed, tumors were collected and dissociated using the homogenizer Precellys evolution of bertin technologies at 6,500 rpm during 2 cycles of 30 s in vials containing ceramic beads. RNA purification was performed using the RNeasy Midi Kit (Qiagen).

SMPD3 expression and mutations in human melanoma: SMPD3 expression was analysed using the TCGA melanoma cohort[32]. TCGA genomic and clinical data were downloaded from the UCSC cancer genome browser project website ("genomecancer.ucsc.edu"). The analysed population consisted in 342 patients with distant metastasis for whom RNAseq and clinical data overlap. Gene expression was measured experimentally using the Illumina HiSeq 2000 RNA Sequencing platform and log 2(x+1) transformed. The strength of relationship between genes was assessed using the Spearman rank correlation coefficient. Date of origin for computation of overall survival was the date to specimen procurement. Survival rates were estimated using Kaplan-Meier method and comparison between groups (low expression vs high expression) was performed using log-rank test. SMPD3 mutation analysis in human melanoma was assessed on cBioportal (www.cbioportal.org/)[33,34] and polyphen2 (genetics.bwh.harvard.edu/pph2/).

Statistical analyses: Results are expressed as means of at least three independent determinations per experiment. Mean values were compared using Student's t-test with Prism software (Graph-Pad). Differences were considered to be statistically significant when P<0.05 (*p<0.05; p<0.01; *p<0.001; n.s.: not significant).

Example 2

Results nSMase 2 is Expressed at Low Levels in Melanoma

We initially performed a meta-analysis on the Oncomine database to evaluate the levels of nSMase 2 transcripts. Data from two independent studies (51, 52) indicated that mRNA encoding nSMase 2 is expressed at low levels in melanoma. Indeed, from the Riker and coworkers' study (51), nSMase 2 was less expressed in cutaneous melanoma than in normal skin or skin carcinomas (data not shown). Interestingly, nSMase 2 mRNA levels were even lower in metastatic melanoma when compared with in situ or cutaneous melanoma (data not shown), indicating that nSMase 2 down-regulation is likely associated with melanoma progression. According to the Wagner et al. study (52), nSMase 2 expression is lower in melanoma cell lines as compared to lung, colorectal or pancreatic cancer cell lines (data not shown). In murine (B16F10 and B16K1) melanoma cell lines, mRNA encoding nSMase 2 was expressed at low levels as evaluated by RT-qPCR and Smpd3 expression was greatly enhanced upon trichostatin A but not 5-Azacytidine treatment (FIG. 1G), indicating that Smpd3 is likely down-regulated in B16 melanoma cell lines in an HDAC-dependent manner.

nSMase 2 Over-Expression Triggers Ceramide Accumulation in B16K1 Melanoma Cell Line.

To evaluate the role of nSMase 2 in B16 melanoma growth, a plasmid encoding a V5-tagged nSMase 2 was transfected into B16K1 melanoma cells, which stably overexpress MHC I molecules. Transfected cells were selected for their resistance towards blasticidin. Clones were isolated by limiting dilution and further characterized for VS-tagged nSMase 2 expression and nSMase activity. One clone, called 2–, did not express VS-tagged nSMase 2, as evaluated by Western blot (FIG. 1A), despite its resistance to the antibiotic. In sharp contrast, another clone, called 2+, robustly expressed VS-tagged nSMase 2 (FIG. 1A). V5-tagged nSMase 2 expression did not alter MHC I expression at the cell surface of B16K1 cells (data not shown). In accordance with Western blot experiments, 2+ cells exhibited a strongly increased nSMase specific enzyme activity as compared to mock-transfected cells and 2– cells (FIG. 1B). Confocal microscopy experiments indicated that VS-tagged nSMase 2 proteins were localized at the plasma membrane in 2+ cells (data not shown). Moreover, 2+ cells displayed a 3-fold increase in intracellular ceramide level as compared to mock-transfected cells or 2– cells (FIG. 1C). Thus, expression of stable VS-tagged nSMase 2 in B16K1 cells is accompanied by a significant accumulation of ceramide.

nSMase 2 Over-Expression Does Not Sffect B16K1 Melanoma Tumorigenic Properties In Vitro.

The production of ceramide, derived from SM breakdown as a consequence of increased nSMase 2 expression, has been reported to inhibit cell growth (26, 27). To evaluate the consequence of nSMase 2 over-expression on B16K1 cell proliferation, we evaluated the cell growth of 2+ and 2– cells under 10% FCS or serum starvation conditions. Cell growth of both clones was similar under both conditions (FIG. 1D). Moreover, their ability to form colonies on soft agar and grow into spheroids was not impaired by nSMase 2 over-expression (data not shown).

To further evaluate the effect of nSMase 2 overexpression in mouse melanoma, B16K1 cells were transduced with a retroviral vector encoding either a WT or catalytically inactive nSMase 2. This approach allowed the generation of cell lines expressing either WT or catalytically inactive nSMase 2, which did not derive from single clones. The transduced cell lines potently expressed WT and catalytically inactive nSMase2 as evaluated by Western blot (FIG. 1E). Immunofluorescence analysis indicated that transduced B16K1 expressed different levels of either WT or catalytically inactive nSMase 2 (data not shown), consistent with the fact that transduced cells are heterogeneous cell populations. Both the WT nSMase 2 and its mutant form were located at the plasma membrane but not at the Golgi apparatus (data not shown). As compared to mock-transduced cells, neutral SMase activity was increased in cells expressing the WT, but not the catalytically inactive nSMase 2 (FIG. 1F). Sphingolipidomic analysis disclosed ceramide accumulation in WT nSMase 2 overexpressing cells (data not shown). However, none of the other SL species, including SM, displayed significant changes in B16K1 nSMase 2 WT cells as compared to their mock counterparts. In vitro growth was comparable for the different cell lines (data not shown), further indicating that nSMase 2 is not a major modulator of B16K1 cell proliferation.

Collectively, our data indicate that nSMase 2 over-expression in B16K1 cells had no consequence on cell growth and tumorigenic properties in vitro despite the intracellular ceramide increase.

nSMase 2 Over-Expression Impairs B16K1 Melanoma Cell Growth In Vivo.

We next evaluated the impact of nSMase 2 over-expression on B16K1 tumor growth in vivo. Wild-type C57Bl/6 mice were challenged by intradermal injection of either 2− or 2+ cells. Interestingly, 2+ cell growth was reduced by 70% as compared to 2− cells, indicating that nSMase 2 over-expression greatly impaired B16K1 growth in WT mice (FIG. 2A, left panel). Three weeks after inoculation, tumors were collected and proteins were extracted to evaluate V5-tagged nSMase 2 expression and nSMase specific enzyme activity. As expected, tumors derived from 2+ cells, but not 2− cells, expressed the V5-tagged nSMase 2 and nSMase activity was consequently increased (data not shown).

To further evaluate the consequence of V5-tagged nSMase 2 expression on SL metabolism, intra-tumor SL levels were determined by mass spectrometry (data not shown). Importantly, V5-tagged nSMase 2 expression was associated with a significant increase of intra-tumor ceramide and sphingosine levels; however, this effect did not extend to the levels of sphingosine-1-phosphate, which remained unaltered (data not shown). Among the different ceramide species, both C16:0 and C24:1 ceramides were significantly increased in tumors expressing V5-tagged nSMase 2 (data not shown).

Since B16K1 cells do express high levels of MHC-I, which restricts antigen recognition by CD8+ T cell, we sought to evaluate whether CD8+ T cells are responsible for the alteration of B16K1 tumor growth upon V5-tagged nSMase 2 expression. Thus, we grafted 2− and 2+ cells in nude and CD8-deficient mice. In sharp contrast to the above observations in WT mice (i.e., immuno-competent mice), nSMase 2 over-expression did not impair the B16K1 tumor growth in nude mice (data not shown) and CD8-deficient mice (FIG. 2A, right panel).

To evaluate whether the nSMase 2-dependent alteration of SL composition is involved in the inhibition of B16K1 melanoma growth, we grafted WT mice with B16K1 cells, which have been transduced with a control retroviral vector (mock) or with retroviral vectors encoding either WT (nSMase 2 WT) or catalytically-inactive nSMase 2 (nSMase 2 C.I.). Whereas the in vivo tumor growth of WT nSMase 2 over-expressing cells was reduced (by more than 50%) as compared to mock transduced B16K1 cells or catalytically-inactive nSMase 2 expressing cells in immunocompetent mice, WT nSMase 2 overexpression did not compromise B16K1 tumor growth in CD8-deficient mice (FIG. 2B).

Collectively, our data indicate that nSMase 2 expression and enzyme activity impair B16K1 melanoma growth in immunocompetent but not immunodeficient mice.

nSMase 2 Over-Expression Enhances T Cell-Dependent Immune Response Towards B16K1 Cells.

We thus hypothesized that nSMase2 over-expression in B16K1 cells enhances the CD8 T cell-dependent immune response towards melanoma. To evaluate this tenet, we initially analyzed the immune response by monitoring the tumor-infiltrating leukocytes (TILs) by flow cytometry. The tumor content of leukocytes (CD45+), T lymphocytes (Thy1+) and, albeit to a lesser extent, Natural Killers (NK1.1+) was significantly enhanced in tumors that over-expressed nSMase 2 (data not shown). In contrast, B lymphocytes (CD19+) were poorly infiltrated into the B16K1 tumors and nSMase 2 over-expression did not modify CD19+ TIL content (data not shown). Moreover, analysis of myeloid cells indicated that tumor-infiltrating macrophages (CD11b+Gr1-F480+) and myeloid-derived suppressor cells (MDSC, Gr1+CD11b+) remained unchanged following nSMase 2 over-expression in melanoma cells (data not shown). Interestingly, among the T cells, whereas the tumor infiltration of CD4+ T cells was slightly increased, the proportion of CD8+ TILs was 3-fold higher in tumors over-expressing nSMase 2 as was the ratio of CD8+ to CD4+ TILs (data not shown).

As ceramide is a putative bioactive molecule in cell death signaling, we evaluated whether nSMase 2 over-expression sensitized B16K1 cells to cell-mediated cytotoxicity. As a matter of fact, 2+ and 2− cells were equally sensitive to cell-mediated cytotoxicity, indicating that nSMase 2 over-expression did not enhance the B16K1 cell death under our experimental conditions (data not shown). Moreover, nSMase 2 overexpression did not sensitize B16K1 cells to some effector molecules of cell-mediated cytotoxicity (i.e., the death receptor ligands CD95L, TRAIL and TNF) (data not shown).

Collectively, our data indicate that nSMase 2 over-expression in B16K1 cells (i) alters tumor SL composition, (ii) facilitates the CD8+ T cell tumor infiltration and, consequently, (iii) inhibits B16K1 tumor growth.

The nSMase 2 Enzyme Activity is Required for Enhancing T Cell-Dependent Anti-Melanoma Response.

The immune response was next analyzed by evaluating TIL content in B16K1 tumors overexpressing either WT or catalytically inactive nSMase 2 (FIG. 3). At day 12 post-injection, the tumor weight was significantly reduced by WT nSMase 2 overexpression (FIG. 3A) and this was associated with an increased CD45+ TIL content (data not shown). Both CD8+ and CD4+ TILs were increased in tumors overexpressing wild-type nSMase 2 (FIG. 3B). We next evaluated the tumor content in CD8+ T cells specific for tyrosinase-related protein 2 (TRP2), a differentiation antigen of melanocytic cells. Using the MHC-I dextramer technology, we showed that the TRP2-specific CD8+ T cell content was higher in tumors overexpressing WT nSMase 2 (FIG. 3C). Analysis of mRNA expression evaluated by RT-qPCR in B16K1 tumors overexpressing WT or CI nSMase 2 showed that mRNA encoding CXCL9 and IFNγ, two major Th1-related cytokines, were significantly increased upon WT nSMase 2 overexpression (FIG. 3D).

Altogether, our data indicate that nSMase 2 catalytic activity is required for enhancing T cell-dependent immune responses towards B16K1 melanoma cells.

The nSMase 2 Enzymatic Activity Enhances the Immunogenicity of Exosomes Produced by Melanoma Cells.

nSMase 2 has recently been shown to facilitate the budding of exosomes, which likely contribute to the modulation of the anti-melanoma immune response. Thus, we have evaluated the consequences of WT or CI nSMase 2 overexpression in B16K1 melanoma cells on exosome secretion and molecular composition. Exosomes were purified from the culture medium of B16K1 cells overexpressing either WT or CI nSMase 2. The quantity of secreted exosomes, as evaluated by total protein determination, the ultra-structural morphology analysed using electron microscopy, as well as the protein composition (tetraspanins, melanoma antigens as evaluated by using western blot and FACS analysis) were similar for both exosome types (FIG. 4A and data not shown). Since nSMase 2 is involved in the exosomal secretion of some miRNA, we next evaluated the exosomal miRNA content, and found that miR-155 was greatly enriched in exosomes secreted by B16K1 cells overexpressing WT nSMase 2 (FIG. 4B). In contrast, the exosomal content of miR-21a and miR-146a was similar in both exosome types (FIG. 4B and data not shown). Considering that exosomes are efficiently uptaken by dendritic cells and miR-155 is a major pro-inflammatory miRNA modulating dendritic cell differentiation, we next analysed the capacity of the exosomes to facilitate dendritic cell maturation. We initially analysed, by flow cytometry, the expression level of dendritic cell surface maturation markers such as CD80, CD86, MHC-I and MHC-II. All those markers were up-regulated to the same extent at the dendritic cell surface following incubation with exosomes from B16K1 overexpressing either WT or C.I nSMase 2 (data not shown). In sharp contrast, the exosomes from B16K1 overexpressing WT nSMase 2 greatly enhanced the intracellular levels of mRNA encoding IL-12, a major pro-Th1 cytokine, and CXCL9, a chemokine facilitating T cell tumor infiltration (FIG. 4C), both of them being induced by IFNγ. This phenomenon was associated with a decrease in cellular amounts of mRNA encoding SOCS1, a major IFNγ signaling repressor, which is a well-known miR-155 target (53) (FIG. 4C). This data indicates that the exosomal miR-155, which is enriched upon WT nSMase 2 overexpression, is biologically active and facilitates the expression of Th1 cytokines. Thus, we hypothesize that nSMase 2 enhances the immunogenicity of exosomes secreted by melanoma cells. To evaluate this tenet, exosomes from B16K1 overexpressing WT or C.I. nSMase 2 were co-injected with parental B16K1 cells in immunocompetent mice. Exosomes from B16K1 overexpressing WT nSMase 2 significantly reduced tumor growth and enhanced CD8+ TIL content as compared to the exosomes from B16K1 overexpressing CI nSMase 2 (FIG. 4D).

Collectively, our data indicate that the nSMase 2 enzymatic activity enhances the immunogenicity of exosomes produced by B16K1 melanoma cells.

nSMase 2 Enzymatic Activity Enhances the Response to Immune Checkpoint Inhibitors.

To further evaluate the role of nSMase 2 in the anti-melanoma immune response, we analysed the consequences of nSMase 2 over-expression on the response to emerging immune therapies (i.e., anti-CTLA-4, anti-PD-1) (FIG. 5). Under our experimental conditions (FIG. 5A), whereas anti-PD-1 and anti-CTLA-4 have limited anti-tumor effects when mice were injected with B16K1 overexpressing the CI nSMase 2, WT nSMase 2 overexpression in B16K1 cells significantly enhanced the response to both antibody treatments (FIG. 5B). The effect was greater towards anti-CTLA-4 antibody and 4 out of 5 mice, which have been grafted with B16K1 overexpressing WT nSMase 2, displayed total tumor regression. Interestingly, those mice did not develop melanoma tumors upon a novel B16K1 injection two months after the first B16K1 graft, indicating that they were fully vaccinated (data not shown).

Altogether, our data indicate that the enzymatic activity of nSMase 2 in B16K1 melanoma enhances the therapeutic response to immune checkpoint inhibitors.

Discussion:

The present study provides evidence for the first time that expressing nSMase 2 in B16K1 mouse melanoma cells facilitates the CD8+ T cell tumor infiltration, thereby slowing down melanoma growth. NSMase 2 overexpression in B16K1 cell lines enhanced CD8+ TIL content and impaired B16K1 tumor growth in wild-type mice (i.e., immunocompetent) but not in mice lacking CD8+ T cells (i.e., nude and CD8-deficient mice).

The mechanisms by which nSMase 2 facilitates the CD8+ T cell-dependent immune response most likely depends on the alteration of intratumor SL content since overexpression of a catalytically inactive nSMase 2 mutant had no effect on B16K1 tumor growth and CD8+ T cell-dependent immune response. Analysis of tumor SL content indicated a significant increase in ceramide levels (from 1 to 1.5 nmol/mg) in tumors overexpressing nSMase 2. Moreover, intra-tumor sphingosine levels also increased upon nSMase 2 overexpression, albeit to a lesser extent (from 20 to 30 pmol/mg). Taking into account that sphingosine facilitates the secretion of RANTES/CCLS (54, 55), which is a potent chemoattractant towards CD8+ T cells, the possibility that the nSMase 2-induced sphingosine increase is involved in CD8+ T cell infiltration cannot be ruled out. In addition, sphingosine is the substrate of sphingosine kinases, which produce S1P, a critical mediator of lymphocyte traffic (33). One should note however, that the levels of intratumor S1P remained unchanged upon nSMase 2 overexpression. Hence, it is unlikely that S1P directly mediates the nSMase 2-triggered increase of CD8+ TIL content.

Detailed analyses of the intracellular SL content in transduced B16K1 cells over-expressing or not wild-type nSMase 2 demonstrated that only the intracellular levels of ceramide increased upon nSMase 2 over-expression. The intracellular concentration of all other SL metabolites, including SM, glycosphingolipids as well as sphingosine and sphingosine-1-phosphate, did not change upon nSMase 2 over-expression. As a matter of fact, SM reduction was observed in B16K1 nSMase 2+ clone, which exhibits a strong neutral SMase activity (180 nmol/h/mg), but not in B16K1 nSMase 2 WT cell lines, which display a much lower neutral SMase activity (20 nmol/h/mg). The increase in CD8+ T cell tumor infiltration and the subsequent tumor growth reduction were found not only for B16K1 nSMase 2+ clone but also for B16K1 nSMase 2 WT cell lines, indicating that the SM reduction, which is only observed in B16K1 exhibiting the highest neutral SMase activity, is unlikely responsible for both phenomena.

The mechanisms by which nSMase 2 facilitates CD8+ TIL content have been investigated. We provide evidence for the first time that nSMase 2 expression enhances the immunogenicity of melanoma cell-derived exosomes by increasing their content in miR-155, a major pro-inflammatory miRNA, which silences SOCS1 mRNA (53), thereby facilitating the increase in IL-12 and CXCL9 mRNA content in dendritic cells. Consequently, we observed an increased level in mRNA encoding IFNγ and CXCL9 in B16K1 tumors overexpressing WT nSMase 2. The increased immunogenicity of melanoma cell-derived exosomes is further documented by the increased CD8+ TIL content and the decreased B16K1 tumor weight upon injection of exosomes derived from B16K1 overexpressing WT nSMase 2. As a matter of fact, nSMase 2 overexpression did not facilitate the exosomal secretion of miR-21a and miR-146, indicating that nSMase 2, and putatively ceramide, may enhance the budding of exosomes, which are enriched in selective miRNA, including miR-155 as documented here as well as miR-210 and miR-10b as reported by others. The mechanisms by which nSMase 2 facilitates the selectivity of the miRNA association to exosomes, remain to be determined.

We provide evidence for the first time that nSMase 2 enzyme activity in melanoma enhances the therapeutic response to emerging immunotherapies (i.e., anti-PD-1, anti-CTLA-4). Monoclonal antibodies inhibiting CTLA-4 (ipilimumab) or PD1 (nivolumab, pembrolizumab) have demonstrated significant efficacy in the treatment of metastatic melanoma, promoting high response rate and long-lasting tumor control. Despite promising results, about 40% of patients do not display therapeutic response and a significant proportion of responders experience tumor relapse within 2 years following treatment induction. It is tempting to speculate that increasing SMPD3 expression and/or the intratumor ceramide level in melanoma tumors may constitute an original therapeutic strategy to improve the efficacy of emerging immunotherapies.

Example 3

Results:

NSMase2 Expression Enhances CD8+ Tumor-Infiltrating Lymphocytes in Melanoma.

Analysis from the Oncomine and TCGA databases indicated that mRNA encoding nSMase2 is expressed at low levels in human metastatic melanoma as compared to primary tumors, suggesting that nSMase2 downregulation is likely associated with melanoma progression. The clinical outcome in metastatic melanoma patients exhibiting high (80th percentile) and low (20th percentile) SMPD3 expression was next analysed. Low SMPD3 expression was statistically associated with shortened overall survival (FIG. 6A), further arguing that SMPD3 downregulation is associated with a bad prognosis in melanoma.

Figure 6A:
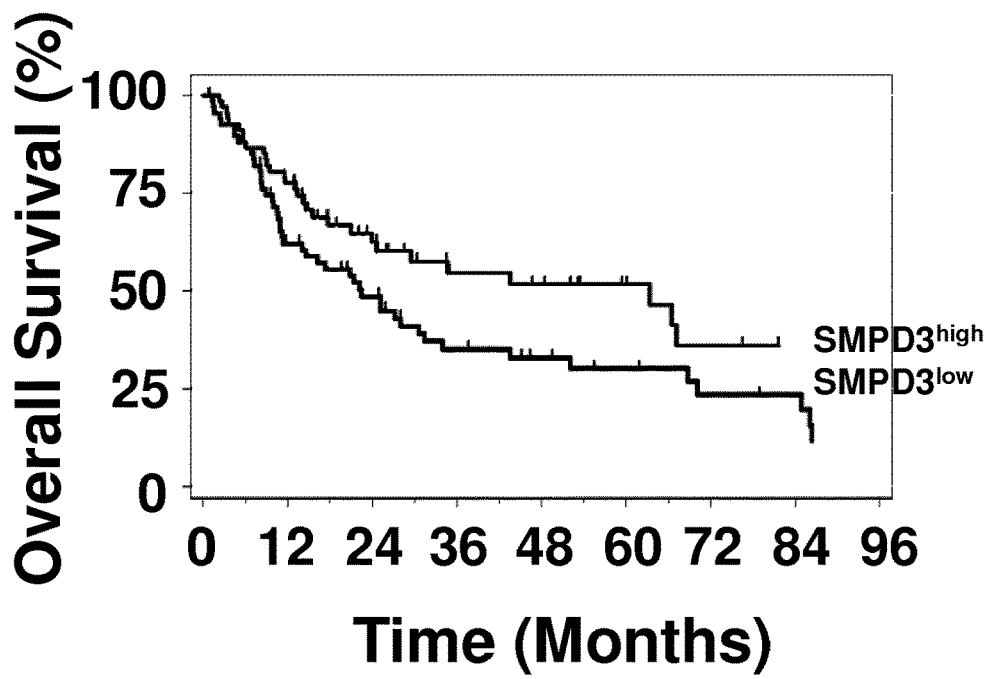
Figure 6B:
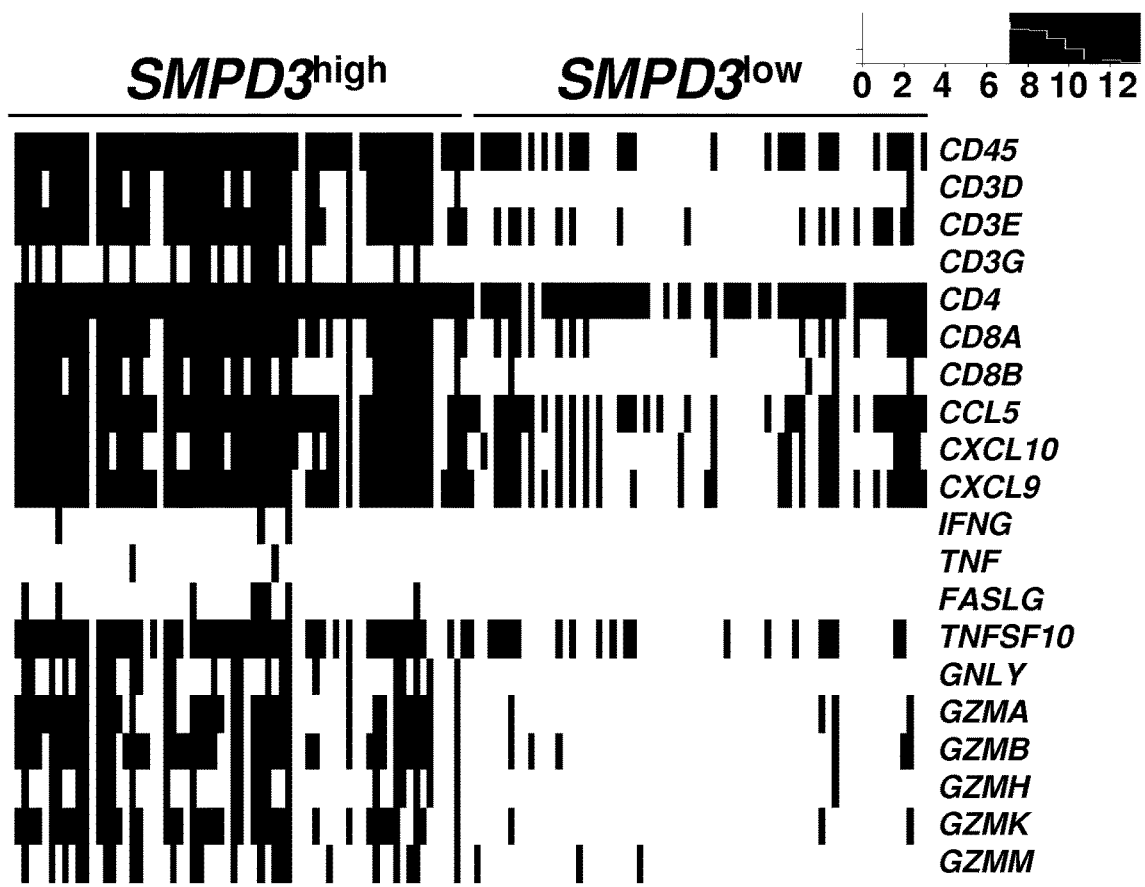
Figure 6C:
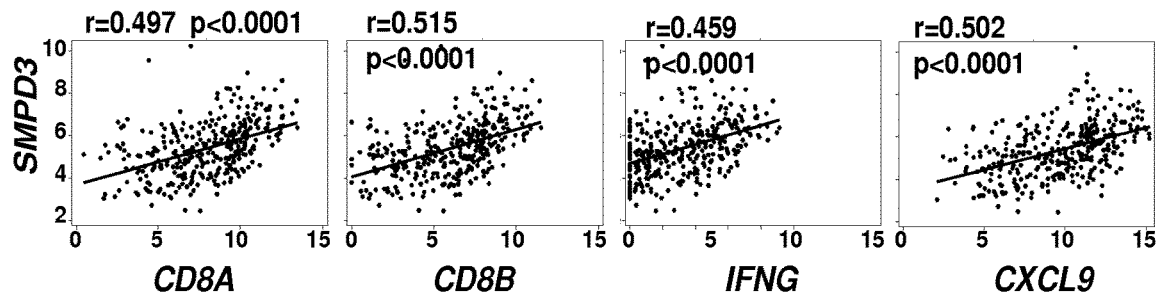

We next analysed the gene signatures in patients from the TCGA melanoma cohort exhibiting high and low SMPD3 expression in melanoma samples. Of great interest was the finding that high SMPD3 expression was mostly associated with the "Immune system process" and "Lymphocyte activation" according to Gene ontology classification. We next identified the genes that were differentially expressed in human melanoma exhibiting either high or low SMPD3 expression in melanoma samples from patients affected with metastatic melanoma (FIG. 6B). High SMPD3 expression was associated with high expression of CD3G, CD3D and CD3E, which reflect tumor-infiltrating T lymphocytes (TIL). Among T cell genes, we found that CD8A, CD8B and CD4 were enriched in melanoma samples expressing SMPD3 at high levels. Moreover, various Th1-related genes such as IFNG, TNF, CXCL9, CXCL10 and CCL5 as well as cell-mediated cytotoxicity genes were highly expressed in melanoma samples exhibiting high SMPD3 expression (FIG. 6B). Accordingly, SMPD3 expression was significantly correlated with the expression of diverse genes, which likely reflects CD8+ T cell infiltration (FIG. 6C). This observation was not restricted to metastatic melanoma since similar correlations were found in triple negative breast cancers (Table 1). Of note, the expression levels of genes encoding the other known sphingomyelinase isoforms were not associated with a gene signature of CD8+ TIL in metastatic melanoma patients, except SMPD2 the expression of which poorly, yet significantly, correlated with that of CD8B. As a matter of fact, SMPD4 was anti-correlated with T cell-related genes. Thus, SMPD3 expression is associated with a signature of CD8+ T cell tumor infiltration in human melanoma samples, and this cannot be extended to the other sphingomyelinase isoforms.

Figure 6D:
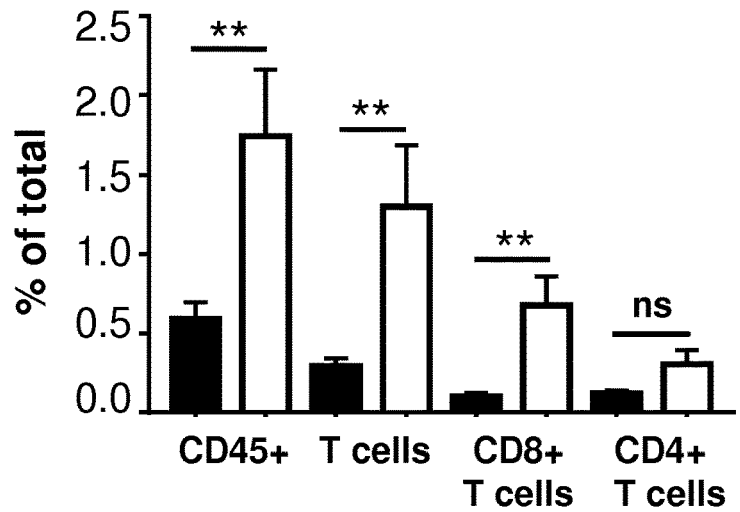
Figure 6E:
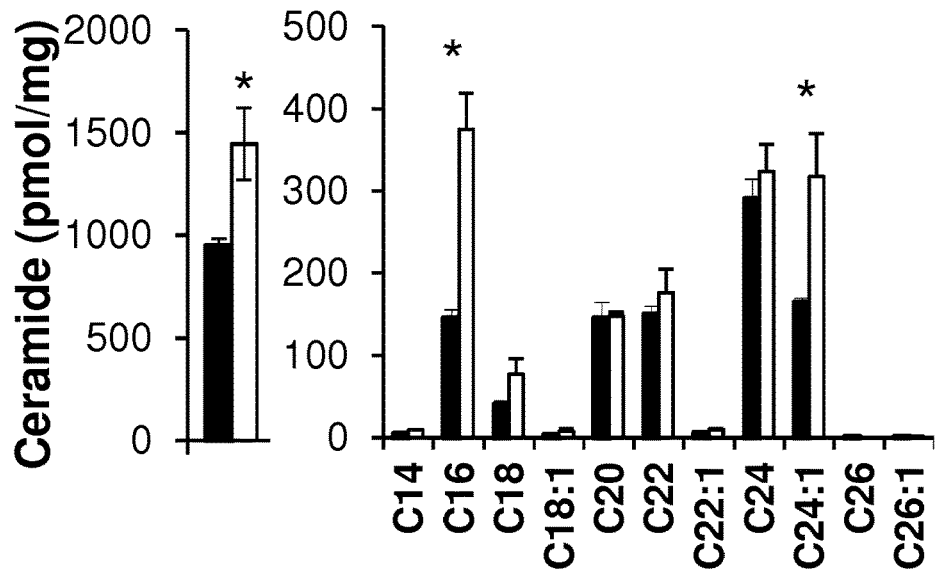

We hypothesized that SMPD3 downregulation contributes to melanoma immune escape with the expression level of nSMase2 being critical for the CD8+ T cell-dependent immune response towards melanoma. To evaluate this tenet, we selected B16K1 (MHC-I$^{high}$) mouse melanoma cell line, which express endogenous nSMase2 at low levels, due to HDAC-dependent epigenetic mechanism. We first generated B16K1 melanoma cell lines overexpressing or not nSMase2. Overexpressed enzyme was mainly located at the plasma membrane and led to robust increase in intracellular neutral sphingomyelinase activity and ceramide level without affecting two- and three-dimensional cell growth in vitro (FIG. 1 and data not shown). We next analysed the immune response in mice grafted with B16K1 melanoma cells expressing nSMase2 at low or high levels. Twelve days after B16K1 cell injection, the tumor content of leukocytes (CD45+) and T lymphocytes (Thy1+) was significantly enhanced in tumors that expressed nSMase2 at high levels (FIG. 6D). Among the T cells, the proportion of CD8+ TILs was 3-fold higher in tumors expressing nSMase2 at high levels (FIG. 6D).

Interestingly, nSMase2 overexpression as evaluated by western blot triggered an intra-tumor increase (i) in the nSMase activity, C16 and C24-ceramides (FIG. 6E) and sphingosine (data not shown) and (ii) a reduction of B16K1 tumor growth in WT mice (FIG. 2A). Of note, no significant changes were noticed for tumor sphingomyelin and S1P content in nSMase2 overexpressing tumors (data not shown). A similar trend was observed in B16F10 melanoma cells in which nSMase2 overexpression significantly reduced tumorigenesis in WT mice without affecting their proliferation rate in vitro (data not shown). Importantly, nSMase2 overexpression failed to impair B16K1 melanoma growth in CD8-deficient mice (FIG. 2A).

Collectively, our data indicate that (i) SMPD3 expression is associated with a CD8+ T cell gene signature in human metastatic melanoma samples, which may translate into improved overall survival and (ii) nSMase2 overexpression in mouse melanoma enhances CD8+ T cell-dependent immunity, which impairs tumor growth.

The nSMase2 Enzyme Activity is Required for Enhancing T Cell-Dependent Anti-Melanoma Immune Response.

Analysis of the SMPD3 nucleotide sequence from 5 independent studies indicated mutations in the coding sequence, ranging from 2.5% to 20% mutation frequency depending on the study. The highest mutation frequency was observed in desmoplastic melanoma, whereas the lowest being in uveal melanoma. Most of the mutations were missense mutations and half of them affected residues in the catalytic domain. Moreover, twelve mutations are predicted to be probably damaging (HumDiv score>0.85) according to PolyPhen-2 analysis. We next evaluated whether a single missense mutation (D428A) into the catalytic domain, which abolished enzyme activity[39], had a putative impact on nSMase2 biological activity in CD8+ T cell-dependent immune response and melanoma growth in mice. B16K1 cells were transduced with a retroviral vector encoding either WT or catalytically-inactive nSMase2. This approach induced a mild expression of both WT and catalytically-inactive nSMase2, leading to significant increase of nSMase activity in WT nSMase2 expressing cells without affecting cell proliferation capacity in vitro nor subcellular localisation. The in vivo tumor growth of WT nSMase2 expressing cells was reduced (by more than 50%) as compared to mock-transduced B16K1 cells or catalytically-inactive nSMase2 expressing cells in syngeneic mice.

The immune response was next analyzed at day 12 post-melanoma B16K1 cell injection. T cells (Thy1+) as well as dendritic cells (DC) (CD11c+) were increased in draining lymph nodes and tumors upon WT nSMase2 expression. Of note, whereas the content of Tregs was increased in lymph nodes, the Treg tumor infiltration was slightly, yet not significantly, enhanced by WT nSMase2 expression. WT nSMase2 overexpression significantly increased CD45+ leukocytes, CD4+ and CD8+ T cells, and DC content in both lymph nodes and tumors and reduced the tumor weight. We next evaluated the tumor content of CD8+ T cells specific for tyrosinase-related protein 2 (TRP2), a differentiation antigen of melanocytic cells. Using the MHC-I dextramer technology, we show that TRP2-specific CD8+ T cell content was higher in tumors expressing WT nSMase2. Of note, the levels of mRNA encoding CXCL9 and IFNγ, two major Th1-related cytokines, were significantly increased upon WT nSMase2 expression in melanoma tumors but not in B16K1 cell culture.

Altogether, our data indicate that nSMase2 catalytic activity is required for enhancing T cell-dependent immune response towards melanoma cells.

nSMase2 Expression in Melanoma Synergises with Immune Checkpoint Inhibitors.

Figure 7C:
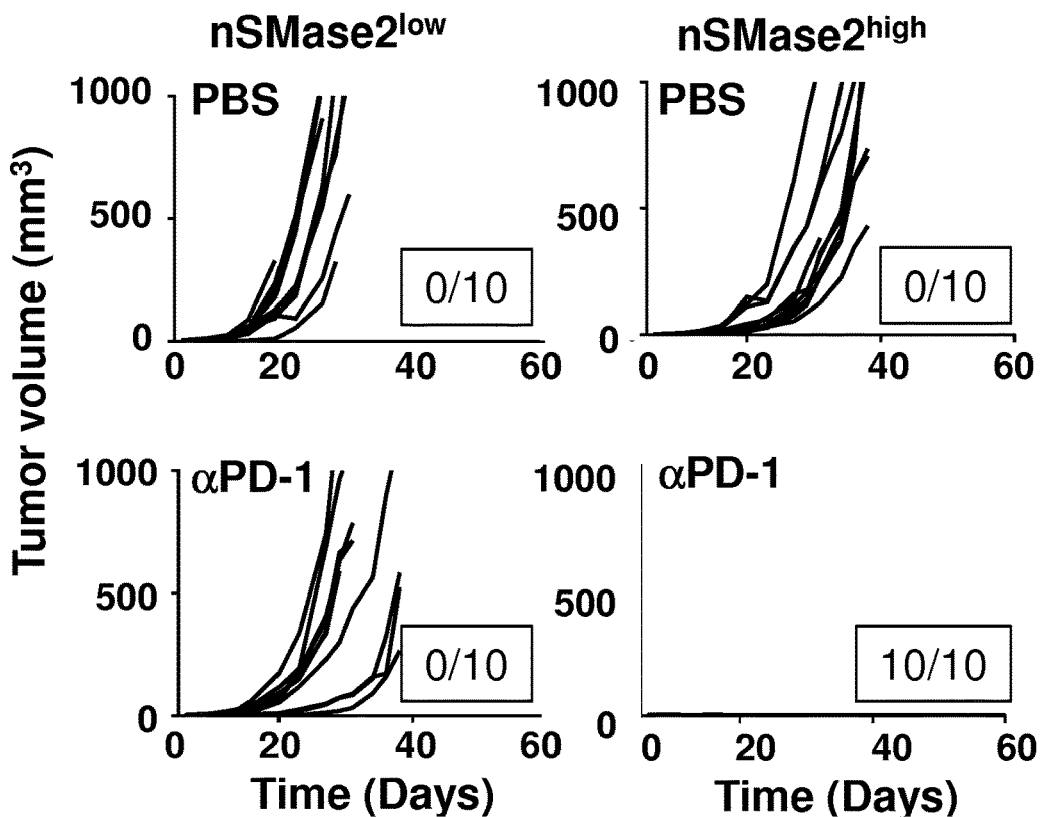
Figure 7D:
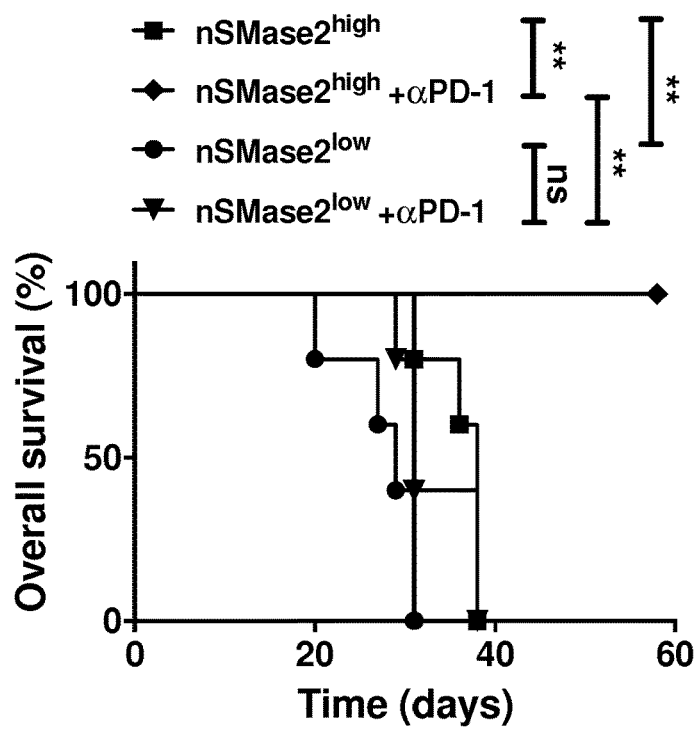

In human melanoma samples, high SMPD3 levels were associated with an increased expression of immunosuppressive genes, such as PDCD1, which encodes the immune checkpoint PD-1 (FIG. 7A). Similar findings were observed in triple negative breast cancers (Table 2). In good agreement with this finding, we observed in mouse melanoma an increased proportion of CD8+ TILs and, albeit to a lesser extent, CD4+ TILs expressing PD-1 in B16K1 tumors expressing WT nSMase2 (FIG. 7B). We next evaluated the therapeutic activity of anti-PD-1 towards melanoma cells expressing nSMase2 at low and high levels. Whereas anti-PD-1 significantly delayed nSMase2$^{low}$ melanoma growth (FIG. 7C), all tumors relapsed presumably due to immune escape mechanisms and, consequently, all mice died within 40 days post-B16K1 injection (FIG. 7D). Moreover, nSMase2 overexpression delayed melanoma growth and slightly, yet significantly, increased the overall survival (FIGS. 7C and 7D). Of major interest, the therapeutic efficacy of anti-PD-1 was dramatically enhanced by nSMase2 overexpression (FIG. 7C). In the group of mice injected with B16K1 nSMase2$^{high}$ and anti-PD-1, all mice survived (FIG. 7D) and none of them developed melanoma upon a second B16K1 cell injection, indicating that they were fully vaccinated against melanoma cells. Our observation was unlikely restricted to anti-PD-1 since WT nSMase2 expression greatly enhanced the therapeutic effect of anti-CTLA-4 blocking antibodies against melanoma.

Altogether, our data indicate that expression of WT nSMase2 in B16K1 melanoma synergizes with immune checkpoint blockade therapies in mice.

Discussion:

The present study provides the first evidence that (i) SMPD3 is expressed at low levels in most human metastatic melanoma samples and (ii) low SMPD3 expression is associated with shortened overall survival in patients. Noteworthy, high SMPD3 expression was associated with "Immune system process" and "Lymphocyte activation". Accordingly, melanoma samples expressing SMPD3 at high levels exhibited gene signature of TILs, including genes encoding cytotoxic CD8+ T cell markers such as CD8A/B, GZMA/B and GNLY. As a matter of fact, the expression of genes (SMPD1, SMPD2, SMPD4) encoding the other sphingomyelinase isoforms did not correlate with TCR signaling pathway. Thus, the distinctive biological properties of nSMase2 in melanoma do not extend to the other sphingomyelinases, presumably due to different subcellular localisation and/or biochemical properties as well as different role in cell signaling[2]. One should note, however, that enforced expression of acid SMase, encoded by Smpd1 in B16F1 melanoma, is associated with an augmentation of CD8+ TIL[15]. The lack of correlation between SMPD1 expression and immune-related gene signature in human metastatic melanoma samples indicates that acid SMase is unlikely a critical modulator of CD8+ T cell-dependent immune response in melanoma patients.

In good agreement with data from human melanoma, nSMase2 heightens the CD8+ T cell dependent immune response, thereby slowing down melanoma growth in mice. Strikingly, nSMase2 overexpression in mouse melanoma cell lines enhanced CD8+ TIL content and impaired melanoma growth in WT animals (i.e., immuno-competent) but not in mice lacking CD8+ T cells (i.e., CD8-deficient mice), demonstrating that nSMase2 anti-tumorigenic properties are fully dependent on its ability to stimulate adaptive immunity. Collectively, our data reveal that SMPD3 downregulation or mutation likely contributes to melanoma immune escape, facilitating melanoma progression.

The mechanisms by which nSMase2 facilitates the CD8+ T cell-dependent immune response most likely rely on the alteration of intratumor SL content since expression of a catalytically inactive nSMase2 mutant had no effect on B16K1 tumor growth. Accordingly, intra-tumor ceramide and sphingosine content was significantly increased in nSMase2-overexpressing melanoma tumors. Taking into account that sphingosine facilitates the secretion of RANTES/CCL5[44,45], which is a potent chemoattractant towards CD8+ T cells, the possibility that the nSMase 2-induced sphingosine increase is involved in CD8+ T cell infiltration cannot be ruled out. In addition, sphingosine is the substrate of sphingosine kinases, which produce S1P, a critical mediator of lymphocyte traffic[46]. One should note however that the levels of intratumor S1P remained unchanged upon nSMase2 overexpression. Hence, it is unlikely that S1P directly mediates the nSMase2-triggered increase of CD8+ TIL content. Another interesting hypothesis is that ceramide, which exhibits some analogy with Lipid A, the biologically active core of lipopolysaccharide[47], may mimic pathogen-associated molecular patterns, facilitating DC maturation and ultimately priming the adaptive immune response.

SMPD3 expression in patients was also associated with the expression of genes encoding immune checkpoints such as PD-1, presumably leading to melanoma immune escape. Accordingly, we observed an increased proportion of CD4+ PD-1+ and CD8+PD-1+ TILs in mouse melanoma tumors, which overexpressed nSMase2. Consequently, whereas nSMase2 overexpression in mouse melanoma significantly delayed melanoma growth, all mice died within 40 days post-melanoma cell injection, which strongly suggests melanoma immune escape. In addition, whereas immune checkpoint inhibitors had limited therapeutic effects towards B16K1 melanoma, both anti-PD-1 and anti-CTLA4 greatly suppressed tumor growth of WT nSMase2 expressing melanoma. These observations demonstrate that melanoma nSMase2 enhances the therapeutic response to emerging immunotherapies.

It is tempting to speculate that targeting SL metabolism in melanoma tumors may constitute an original therapeutic strategy to overcome resistance of melanoma, and possibly other cancer types, to emerging immunotherapies. In addition, SMPD3 expression in melanoma samples may serve as a novel biomarker to predict survival and response to immunotherapy.

Tables:

Table 1: correlation between SMPD3 and various genes of immunoactivation in human TNBC (*p<0.05; p<0.01; *p<0.001):

The invention claimed is:

1. A method of enhancing the CD8+ T cell-dependent immune response in a subject suffering from cancer characterized by a low tumor infiltration of CD8+ T cells, said method comprising administering to the subject a therapeutically effective amount of a vector comprising a polynucleotide encoding a neutral sphingomyelinase 2 (nSMase 2) polypeptide, wherein said nSMase 2 polypeptide is capable of increasing intra-tumoral ceramide content, wherein the CD8+ T cell-dependent immune response is enhanced.

2. The method of claim 1, wherein the subject suffers from a cancer selected from the group consisting of neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

3. The method of claim 1, wherein the subject suffers from a melanoma, a melanoma resistant to BRAF inhibitors, or a melanoma with elevated plasma lactate dehydrogenase (LDH).

4. A method of treating cancer characterized by a low tumor infiltration of CD8+ T cells in a subject in need thereof, said method comprising administering to the subject a therapeutically effective combination of an immune checkpoint inhibitor and a vector comprising a polynucleotide encoding a neutral sphingomyelinase 2 (nSMase 2) polypeptide, wherein said nSMase 2 polypeptide is capable of increasing intra-tumoral ceramide content, wherein administration of the combination results in enhanced therapeutic efficacy relative to the administration of the immune checkpoint inhibitor alone, wherein the cancer is treated.

5. The method of claim 4, wherein the immune checkpoint inhibitor is an antibody selected from the group consisting of anti-CTLA4 antibodies, anti-PD-1 antibodies, anti-PD-L1 antibodies, anti-PD-L2 antibodies anti-TIM-3 antibodies, anti-LAG3 antibodies, anti-B7H3 antibodies, anti-B7H4 antibodies, anti-BTLA antibodies, and anti-B7H6 antibodies.

6. A method of treating cancer in a subject in need thereof comprising i) quantifying the density of CD8+ T cells in a tumor tissue sample obtained from the subject, ii) comparing the density quantified at step i) with a predetermined reference value established by measurement of cell densities in historical patient samples, and iii), and when the density quantified at step i) is lower than the predetermined reference value, administering to the subject a therapeutically effective amount of a vector comprising a polynucleotide encoding a neutral sphingomyelinase 2 (nSMase 2) polypeptide, wherein said nSMase 2 polypeptide is capable of increasing intra-tumoral ceramide content, wherein said cancer is treated.

7. A method of treating cancer in a subject in need thereof comprising i) quantifying the density of CD8+ T cells in a tumor tissue sample obtained from the subject ii) comparing the density quantified at step i) with a predetermined reference value established by measurement of cell densities in historical patient samples, and iii) and when the density quantified at step i) is lower than the predetermined reference value, administering to the subject a therapeutically effective combination of an immune checkpoint inhibitor and a vector comprising a polynucleotide encoding a neutral sphingomyelinase 2 (nSMase 2) polypeptide when the density quantified at step i) is lower than the predetermined reference value, wherein said nSMase 2 polypeptide is capable of increasing intra-tumoral ceramide content, wherein administration of the combination results in enhanced therapeutic efficacy relative to the administration of the immune checkpoint inhibitor alone, and wherein said cancer is treated.

8. A method of enhancing the potency of an immune checkpoint inhibitor administered to a subject as part of a treatment regimen, the method comprising administering a pharmaceutically effective amount of a vector comprising a polynucleotide encoding a neutral sphingomyelinase 2 (nSMase 2) polypeptide and the immune checkpoint inhibitor to a subject, wherein said nSMase 2 polypeptide is capable of increasing intra-tumoral ceramide content, and wherein administration of the combination results in enhanced therapeutic efficacy relative to the administration of the immune checkpoint inhibitor alone.

* * * * *

SEQUENCE LISTING

<160> NUMBER OF SEQ ID NOS: 2

<210> SEQ ID NO 1
<211> LENGTH: 655
<212> TYPE: PRT
<213> ORGANISM: Homo sapiens

<400> SEQUENCE: 1

Met Val Leu Tyr Thr Thr Pro Phe Pro Asn Ser Cys Leu Ser Ala Leu
1               5                   10                  15

His Cys Val Ser Trp Ala Leu Ile Phe Pro Cys Tyr Trp Leu Val Asp
            20                  25                  30

Arg Leu Ala Ala Ser Phe Ile Pro Thr Thr Tyr Glu Lys Arg Gln Arg
        35                  40                  45

Ala Asp Asp Pro Cys Cys Leu Gln Leu Leu Cys Thr Ala Leu Phe Thr
    50                  55                  60

Pro Ile Tyr Leu Ala Leu Leu Val Ala Ser Leu Pro Phe Ala Phe Leu
65                  70                  75                  80

Gly Phe Leu Phe Trp Ser Pro Leu Gln Ser Ala Arg Arg Pro Tyr Ile
                85                  90                  95

Tyr Ser Arg Leu Glu Asp Lys Gly Leu Ala Gly Ala Ala Leu Leu
            100                 105                 110

Ser Glu Trp Lys Gly Thr Gly Pro Gly Lys Ser Phe Cys Phe Ala Thr
        115                 120                 125

Ala Asn Val Cys Leu Leu Pro Asp Ser Leu Ala Arg Val Asn Asn Leu
    130                 135                 140

Phe Asn Thr Gln Ala Arg Ala Lys Glu Ile Gly Gln Arg Ile Arg Asn
145                 150                 155                 160

Gly Ala Ala Arg Pro Gln Ile Lys Ile Tyr Ile Asp Ser Pro Thr Asn
                165                 170                 175

Thr Ser Ile Ser Ala Ala Ser Phe Ser Ser Leu Val Ser Pro Gln Gly
            180                 185                 190

Gly Asp Gly Val Ala Arg Ala Val Pro Gly Ser Ile Lys Arg Thr Ala
        195                 200                 205

Ser Val Glu Tyr Lys Gly Asp Gly Gly Arg His Pro Gly Asp Glu Ala
    210                 215                 220

Ala Asn Gly Pro Ala Ser Gly Asp Pro Val Asp Ser Ser Ser Pro Glu
225                 230                 235                 240

Asp Ala Cys Ile Val Arg Ile Gly Gly Glu Glu Gly Gly Arg Pro Pro
                245                 250                 255

Glu Ala Asp Asp Pro Val Pro Gly Gly Gln Ala Arg Asn Gly Ala Gly
            260                 265                 270

Gly Gly Pro Arg Gly Gln Thr Pro Asn His Asn Gln Asp Gly Asp
        275                 280                 285

Ser Gly Ser Leu Gly Ser Pro Ser Ala Ser Arg Glu Ser Leu Val Lys
    290                 295                 300

Gly Arg Ala Gly Pro Asp Thr Ser Ala Ser Gly Glu Pro Gly Ala Asn
305                 310                 315                 320

Ser Lys Leu Leu Tyr Lys Ala Ser Val Val Lys Lys Ala Ala Ala Arg
                325                 330                 335

Arg Arg Arg His Pro Asp Glu Ala Phe Asp His Glu Val Ser Ala Phe
            340                 345                 350

Phe Pro Ala Asn Leu Asp Phe Leu Cys Leu Gln Glu Val Phe Asp Lys
        355                 360                 365

-continued

Arg Ala Ala Thr Lys Leu Lys Glu Gln Leu His Gly Tyr Phe Glu Tyr
370                 375                 380

Ile Leu Tyr Asp Val Gly Val Tyr Gly Cys Gln Gly Cys Cys Ser Phe
385                 390                 395                 400

Lys Cys Leu Asn Ser Gly Leu Leu Phe Ala Ser Arg Tyr Pro Ile Met
                405                 410                 415

Asp Val Ala Tyr His Cys Tyr Pro Asn Lys Cys Asn Asp Asp Ala Leu
                420                 425                 430

Ala Ser Lys Gly Ala Leu Phe Leu Lys Val Gln Val Gly Ser Thr Pro
            435                 440                 445

Gln Asp Gln Arg Ile Val Gly Tyr Ile Ala Cys Thr His Leu His Ala
450                 455                 460

Pro Gln Glu Asp Ser Ala Ile Arg Cys Gly Gln Leu Asp Leu Leu Gln
465                 470                 475                 480

Asp Trp Leu Ala Asp Phe Arg Lys Ser Thr Ser Ser Ser Ala Ala
                485                 490                 495

Asn Pro Glu Glu Leu Val Ala Phe Asp Val Val Cys Gly Asp Phe Asn
            500                 505                 510

Phe Asp Asn Cys Ser Ser Asp Asp Lys Leu Glu Gln Gln His Ser Leu
                515                 520                 525

Phe Thr His Tyr Arg Asp Pro Cys Arg Leu Gly Pro Gly Glu Glu Lys
530                 535                 540

Pro Trp Ala Ile Gly Thr Leu Leu Asp Thr Asn Gly Leu Tyr Asp Glu
545                 550                 555                 560

Asp Val Cys Thr Pro Asp Asn Leu Gln Lys Val Leu Glu Ser Glu Glu
                565                 570                 575

Gly Arg Arg Glu Tyr Leu Ala Phe Pro Thr Ser Lys Ser Ser Gly Gln
            580                 585                 590

Lys Gly Arg Lys Glu Leu Leu Lys Gly Asn Gly Arg Arg Ile Asp Tyr
            595                 600                 605

Met Leu His Ala Glu Glu Gly Leu Cys Pro Asp Trp Lys Ala Glu Val
            610                 615                 620

Glu Glu Phe Ser Phe Ile Thr Gln Leu Ser Gly Leu Thr Asp His Leu
625                 630                 635                 640

Pro Val Ala Met Arg Leu Met Val Ser Ser Gly Glu Glu Glu Ala
                645                 650                 655

<210> SEQ ID NO 2
<211> LENGTH: 1968
<212> TYPE: DNA
<213> ORGANISM: Homo sapiens

<400> SEQUENCE: 2
atggttttgt acacgacccc ctttcctaac agctgtctgt ccgccctgca ctgtgtgtcc      60
tgggccctta tctttccatg ctactggctg gtggaccggc tcgctgcctc cttcataccc     120
accacctacg agaagcgcca gcgggcagac gacccgtgct gcctgcagct gctctgcact     180
gccctcttca cgcccatcta cctggccctc ctggtggcct cgctgccctt gcgtttctc     240 ggctttctct ctggtccccc actgcagtcg gcccgccggc cctacatcta ttcacggctg     300
gaagacaagg gcctggccgg tgggcagcc ctgctcagtg aatggaaggg cacggggcct     360
ggcaaaagct tctgctttgc cactgccaac gtctgcctcc tgcccgactc actcgccagg     420
gtcaacaacc tttttaacac ccaagcgcgg gccaaggaga tcgggcagag aatccgcaat     480
ggggccgccc ggccccagat caaaatttac atcgactccc ccaccaatac ctccatcagc     540

```
gccgctagct tcagcagcct ggtgtcacca cagggcggcg atggggtggc ccgggccgtc      600
cccgggagca ttaagaggac agcctctgtg gagtacaagg gtgacggtgg gcggcacccc      660
ggtgacgagg ctgccaacgg cccagcctct ggggaccctg tcgacagcag cagcccggag      720
gatgcctgca tcgtgcgcat cggtggcgag gagggcggcc ggccacctga agctgacgac      780
cctgtgcctg ggggccaggc caggaacgga gctggcgggg gcccaagggg ccagacgccc      840
aaccataatc agcaggacgg ggattcaggg agcctgggca gcccctcggc ctcccgggag      900
tccctggtga aggggcgagc tgggccagac accagtgcca gcggggagcc aggtgccaac      960
agcaagctcc tgtacaaggc ctcggtggtg aagaaggcgg ctgcacgcag gaggcggcac     1020
cccgacgagg ccttcgacca tgaggtctcc gccttcttcc ccgccaacct ggacttcctg     1080
tgcctgcagg aggtgtttga caagcgagca gccaccaaat tgaaagagca gctgcacggc     1140
tacttcgagt acatcctgta cgacgtcggg gtctacggct gccagggctg ctgcagcttc     1200
aagtgtctca acagcggcct cctctttgcc agccgctacc ccatcatgga cgtggcctat     1260
cactgttacc ccaacaagtg taacgacgat gccctggcct ctaagggagc tctgtttctc     1320
aaggtgcagg tgggaagcac acctcaggac caaagaatcg tcgggtacat cgcctgcaca     1380
cacctgcatg ccccgcaaga ggacagcgcc atccggtgtg ggcagctgga cctgcttcag     1440
gactggctgg ctgatttccg aaaatctacc tcctcgtcca gcgcagccaa ccccgaggag     1500
ctggtggcat ttgacgtcgt ctgtggagat ttcaactttg ataactgctc ctctgacgac     1560
aagctggagc agcaacactc cctgttcacc cactacaggg acccctgccg cctggggcct     1620
ggtgaggaga agccgtgggc catcggtact ctgctggaca cgaacggcct gtacgatgag     1680
gatgtgtgca cccccgacaa cctgcagaag gtcctggaga gtgaggaggg ccgcagggag     1740
tacctggcgt ttcccaccag caagagctcg ggccagaagg ggcggaagga gctgctgaag     1800
ggcaacggcc ggcgcatcga ctacatgctg catgcagagg aggggctgtg cccagactgg     1860
aaggccgagt ggaagaatt cagttttatc acccagctgt ccggcctgac ggaccacctg     1920
ccagtagcca tgcgactgat ggtgtcttcg ggggaggagg aggcatag              1968
```